US012678240B2

(12) United States Patent
Ikits et al.

(10) Patent No.: US 12,678,240 B2
(45) Date of Patent: Jul. 14, 2026

(54) ROBOTIC SURGERY SYSTEM WITH PLAN-DEPENDENT SURGICAL VISUALIZATION

(71) Applicant: MAKO Surgical Corp., Weston, FL (US)

(72) Inventors: Milan Ikits, Weston, FL (US); John Paulus, Pembroke Pines, FL (US); Ajeet Singh Yadav, Weston, FL (US); Curtis McClarin, Saint Cloud, FL (US)

(73) Assignee: MAKO Surgical Corp., Weston, FL (US)

( * ) Notice: Subject to any disclaimer, the term of this patent is extended or adjusted under 35 U.S.C. 154(b) by 280 days.

(21) Appl. No.: 18/216,506

(22) Filed: Jun. 29, 2023

(65) Prior Publication Data

US 2025/0000591 A1     Jan. 2, 2025

Related U.S. Application Data

(60) Provisional application No. 63/357,118, filed on Jun. 30, 2022.

(51) Int. Cl.
*A61B 34/30*          (2016.01)
*A61B 34/10*          (2016.01)
*A61B 34/20*          (2016.01)

(52) U.S. Cl.
CPC .............. *A61B 34/30* (2016.02); *A61B 34/10* (2016.02); *A61B 2034/105* (2016.02); *A61B 2034/107* (2016.02); *A61B 2034/2059* (2016.02)

(58) Field of Classification Search
CPC ... A61B 34/30; A61B 34/10; A61B 2034/105; A61B 2034/107; A61B 2034/2059; A61B 2034/2055; G06T 15/06; G06T 2210/62; G06T 2219/008; G06T 2219/2021
USPC ......... 700/245; 345/420, 424, 419; 606/128; 703/11; 83/768; 701/436
See application file for complete search history.

(56) References Cited

U.S. PATENT DOCUMENTS

| | | | | |
|---|---|---|---|---|
| 5,548,694 | A * | 8/1996 | Frisken Gibson | ...... G06T 15/10 |
| 8,847,954 | B1 * | 9/2014 | Lin | ........................... G06T 7/55 |
| 8,958,611 | B2 | 2/2015 | Ikits | |
| 10,117,713 | B2 | 11/2018 | Moctezuma De La Barrera et al. | |
| 10,660,711 | B2 | 5/2020 | Moctezuma De La Barrera et al. | |
| 11,114,199 | B2 | 9/2021 | Moctezuma De La Barrera | |
| 2004/0102866 | A1 * | 5/2004 | Harris | ..................... G06T 17/00 |

(Continued)

FOREIGN PATENT DOCUMENTS

| | | | | |
|---|---|---|---|---|
| EP | | 3470040 B1 * | 3/2022 | ......... A61B 17/1675 |

OTHER PUBLICATIONS

Yan, Y., Li, Q., Wang, Q. et al. Real-time bone sawing interaction in orthopedic surgical simulation based on the volumetric object. J Vis 21, 239â252 (2018). https://doi.org/10.1007/s12650-017-0455-1 (Year: 2018).*

(Continued)

*Primary Examiner* — Ellis B. Ramirez
(74) *Attorney, Agent, or Firm* — FOLEY & LARDNER LLP

(57) ABSTRACT

A surgical system includes a tool operable to modify a bone and circuitry programmed to orient a voxel grid relative to a model of the bone based on a planned bone modification and generate, using the voxel grid, a visualization of progress of the tool in executing the planned bone modification based on tracking data indicative of positions of the tool.

21 Claims, 19 Drawing Sheets

(56) References Cited

U.S. PATENT DOCUMENTS

| | | | |
|---|---|---|---|
| 2004/0157188 A1 | 8/2004 | Luth et al. | |
| 2007/0038059 A1* | 2/2007 | Sheffer | A61B 90/36 |
| 2008/0266293 A1 | 10/2008 | Cohen | |
| 2009/0160855 A1 | 6/2009 | Wu | |
| 2010/0041004 A1* | 2/2010 | Meglan | G09B 23/283 |
| 2010/0054567 A1* | 3/2010 | Hillebrand | G06T 11/006 |
| 2011/0115787 A1 | 5/2011 | Kadlec | |
| 2011/0257653 A1 | 10/2011 | Hughes et al. | |
| 2013/0172904 A1 | 7/2013 | Ikits | |
| 2015/0277436 A1 | 10/2015 | Kalmar-Nagy et al. | |
| 2015/0331576 A1 | 11/2015 | Piya et al. | |
| 2016/0228204 A1 | 8/2016 | Quaid et al. | |
| 2018/0126553 A1 | 5/2018 | Corkum et al. | |
| 2019/0122330 A1 | 4/2019 | Saget et al. | |
| 2019/0133791 A1 | 5/2019 | Yadav et al. | |
| 2019/0183580 A1* | 6/2019 | Ralovich | A61B 34/10 |
| 2020/0078100 A1 | 3/2020 | Weinstein et al. | |
| 2020/0211698 A1* | 7/2020 | Douglas | G16H 50/50 |
| 2020/0261297 A1 | 8/2020 | Strydom et al. | |
| 2020/0323540 A1 | 10/2020 | Kang et al. | |
| 2021/0077193 A1 | 3/2021 | Ralovich et al. | |
| 2021/0093400 A1 | 4/2021 | Quaid et al. | |
| 2021/0282858 A1 | 9/2021 | Hill et al. | |
| 2021/0338341 A1 | 11/2021 | Malackowski | |
| 2021/0378753 A1* | 12/2021 | Christen | A61B 34/10 |
| 2022/0151703 A1 | 5/2022 | Vandyken | |
| 2023/0053668 A1 | 2/2023 | Malackowski et al. | |

OTHER PUBLICATIONS

International Search Report and Written Opinion for International Application No. PCT/US2023/026596, mailed Oct. 5, 2023, 17 pages.

Amanatides et al., A Fast Voxel Traversal Algorithm for Ray Tracing, Department of Computer Science, University of Toronto, Aug. 1987, 6 pages.

International Search Report and Written Opinion for International Application No. PCT/US2018/065478, mailed Apr. 2, 2019, 9 pages.

* cited by examiner

1400

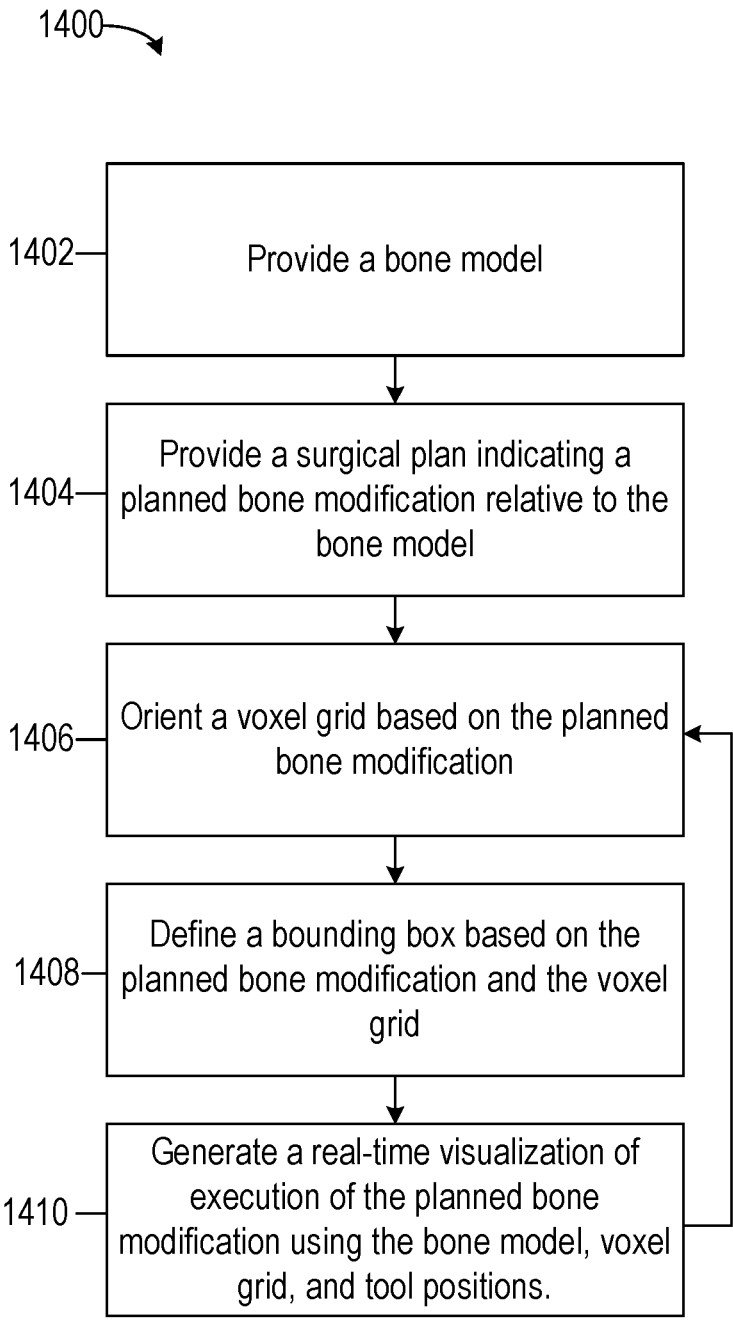

1402 — Provide a bone model

1404 — Provide a surgical plan indicating a planned bone modification relative to the bone model 1406 — Orient a voxel grid based on the planned bone modification 1408 — Define a bounding box based on the planned bone modification and the voxel grid 1410 — Generate a real-time visualization of execution of the planned bone modification using the bone model, voxel grid, and tool positions.

1902 — Determine the surface normals of the modified bone surface at multiple points 1904 — Calculate adjusted normals based on the surface normals of the cut surface and a planned normal from the surgical plan 1906 — Generate a real-time visualization of the execution of the planned bone modification using the adjusted normals

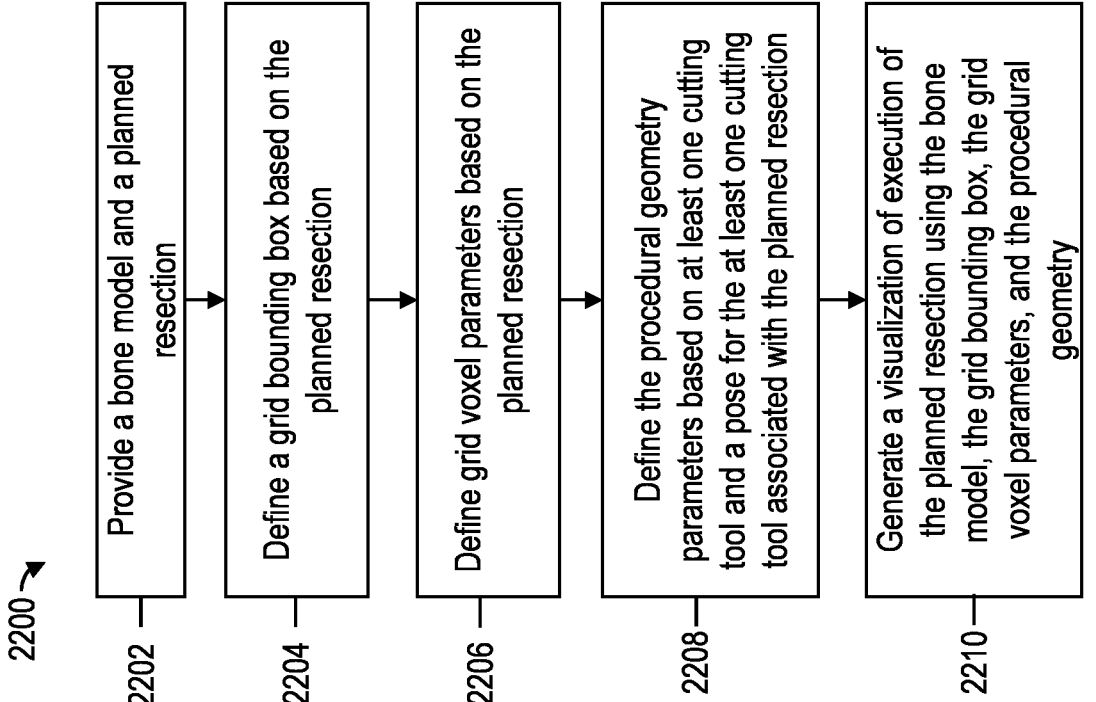

2200

2202 — Provide a bone model and a planned resection

2204 — Define a grid bounding box based on the planned resection

2206 — Define grid voxel parameters based on the planned resection

2208 — Define the procedural geometry parameters based on at least one cutting tool and a pose for the at least one cutting tool associated with the planned resection 2210 — Generate a visualization of execution of the planned resection using the bone model, the grid bounding box, the grid voxel parameters, and the procedural geometry

2402 — Identify fragments along a ray

2404 — Evaluate fragments based on selected transparency rules

2406 — Order fragments

2408 — Provide pixel color based on blending fragments based on ordering

ROBOTIC SURGERY SYSTEM WITH PLAN-DEPENDENT SURGICAL VISUALIZATION

CROSS-REFERENCE TO RELATED APPLICATION

This application claims priority to and the benefit of U.S. Provisional Patent Application No. 63/357,118 filed Jun. 30, 2022, the entire disclosure of which is incorporated by reference herein.

BACKGROUND

The present disclosure generally relates to methods and systems for providing a visual representation of a cut procedure and, more specifically, to computer-implemented methods and systems for providing a visual representation of material removal from an object during a cut procedure.

The transformation of a cut procedure into a visual representation is of interest in many applications such as surgery, machining, and milling. For example, there is an interest in developing and improving systems and methods for providing a visual representation of surgical resection procedures as a cutting tool (e.g., burr, saw, reamer, etc.) is penetrating the bone or tissue of a patient. More particularly, providing real time (or perceived real time) updates of the progress of bone or tissue removal at a display screen allows a surgeon or other medical staff to visualize material removal from the bone or tissue as the cutting tool penetrates the bone or tissue.

Visualization of a resection procedure can be computationally expensive, in some cases resulting in delays that provide a lag between actual progress of bone or tissue removal and graphical updates at a display screen. Additionally, even if a cutting tool travels along a smooth, continuous path during the resection procedure, visualizations can often have visual artifacts such as edgy, ridge-like patterns that do not accurately represent resected surfaces.

Thus, innovations for providing a visual representation of material removal during a cut procedure, such as a bone resection procedure, which reduce computational expense while reducing visualization artifacts are desirable.

SUMMARY

One implementation of the present disclosure is a method. The method includes providing a virtual bone model and a surgical plan defining a planned cut relative to the virtual bone model, orienting a voxel grid relative to the bone model based on the planned cut, obtaining tracking data indicative of positions of a cutting tool, and providing guidance for execution of the planned cut by generating a visualization based on the voxel grid and the tracking data.

Another implementation of the present disclosure is one or more non-transitory computer-readable media storing program instructions that, when executed by one or more processors, cause the one or more processors to perform operations. The operations include providing a bone model and a surgical plan defining a planned cut relative to the virtual bone model and orienting the bone model relative to a graphics coordinate system based on the planned cut such that the planned cut is orthogonal to a first dimension of the graphics coordinate system, parallel to a second dimension of the graphics coordinate system, and parallel to a third dimension of the graphics coordinate system. The operations also include generating a visualization of execution of the planned cut based on the graphics coordinate system, the bone model, and tracking data indicative of positions of a cutting tool during the execution of the planned cut.

Another implementation of the present disclosure is a surgical system. The surgical system includes a tool operable to modify a bone. The surgical system also includes circuitry programmed to orient a voxel grid relative to a model of the bone based on a planned bone modification and generate, using the voxel grid, a visualization of progress of the tool in executing the planned bone modification based on tracking data indicative of positions of the tool.

BRIEF DESCRIPTION OF THE FIGURES

FIG. 14 is a flowchart of a plan-dependent visualization process, according to some embodiments.

FIG. 22 is a flowchart of a process for generating a visualization using procedural geometry, according to some embodiments.

Figure 1:
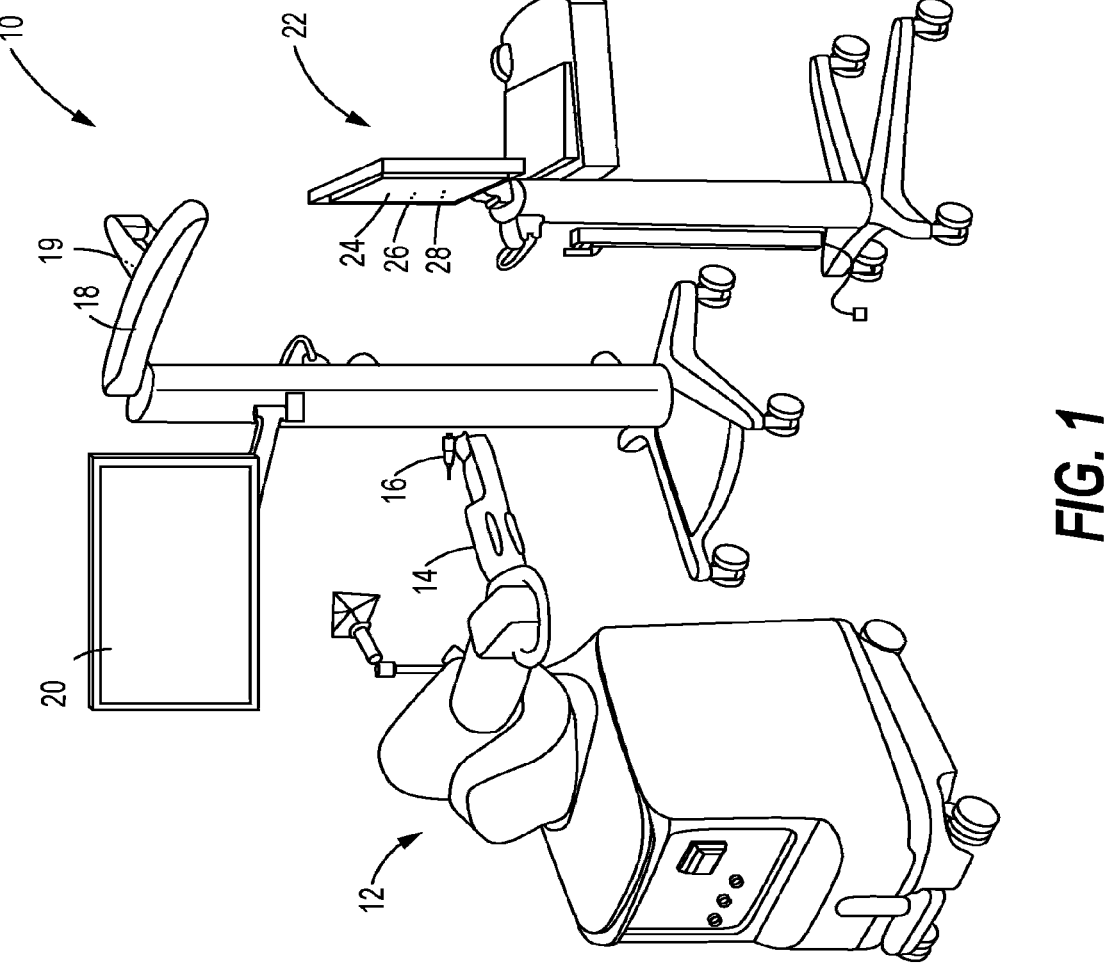
FIG. 1 is a perspective view of a system configured to provide a visual representation of material removal from an object by a cutting tool during a cut procedure, constructed in accordance with the present disclosure.

It should be understood that the drawings are not necessarily drawn to scale. It is to be further appreciated that the following detailed description is merely exemplary in nature and is not intended to limit the invention or the application and uses thereof. Hence, although the present disclosure is, for convenience of explanation, depicted and described as certain illustrative embodiments, it will be appreciated that it can be implemented in various other types of embodiments and in various other systems and environments.

DETAILED DESCRIPTION

The present disclosure relates to methods and systems for providing a visual representation of material removal from an object by a cutting tool during a cut procedure. For example, the method and system disclosed herein may be used to provide a visual representation of the progress of bone material removal from bone during a surgical bone resection procedure. In other non-limiting examples, the method and system disclosed herein may be used provide a visual representation of material removal in a machining or milling operation. The visual representation may be provided at a display that is updated continuously as the cutting tool penetrates the object so that a user (e.g., a surgeon, etc.) can monitor the progress of material removal in real time (perceived real time). This allows the user to confirm that the planned volume of the object has been removed and obtain a notification if the cutting tool penetrates beyond the planned volume (and a visualization of such penetration). Below is a list of terms and phrases used throughout the present disclosure and their meanings as used herein, many or all of which are apparent to those with ordinary skill in the art.

Constructive solid geometry (CSG): a technique for displaying complex geometrical models by combining multiple models using mathematical operations, such as the Boolean set operations of union, intersection, and subtraction.

CSG operations: the mathematical operations used to combine multiple models to display complex geometrical models, such as the Boolean set operations of union, intersection, and subtraction.

Voxel: volumetric pixel (the volumetric equivalent of a pixel); each of an array of discrete elements into which a representation of a three-dimensional object is divided. Each voxel has a 3D coordinate and holds the color at that coordinate.

Object space: represented in a three-dimensional voxelized grid.

Rasterization: concept in computer graphics describing how a polygonal geometry is converted into a raster (pixel or voxel) image.

A-Buffer rasterization: a visible surface detection technique used to identify what is visible in a scene from a specific viewing point of a virtual camera; an extension of the Z-buffer method which adds transparency. A-buffer rasterization creates an A-buffer containing values describing the depth complexity of the scene.

Fragment: one of a plurality of surfaces making up a pixel and contributing to the color of the pixel.

Cut trajectory: a path that a cutting tool follows during a cut procedure; the volume that the cutting tool has swept through the object up to the current point in time.

Referring now to the drawings, and with specific reference to FIG. 1, a system 10 for performing a cut procedure on an object and providing a visual representation of material removal from the object during the cut procedure is shown. As a non-limiting example, the cut procedure may be a surgical tissue or bone resection procedure, such as a hip or knee arthroplasty. Alternatively, the cutting procedure may be a machining or milling procedure. The system 10 may include a robot system 12 having a robotic arm 14 that holds and moves a cutting tool 16 (e.g., a burr, saw, reamer, etc.) during the cut procedure. The system 10 may further include a tracking device 18 having an optical localization system 19 (including an optical localization camera) that tracks the poses (positions/orientations) of the cutting tool 16 and the object to be cut (e.g., bone, etc.) during the cutting procedure. The tracking device 18 may be positioned at a stand or at another location separate from the robot system 12, or it may be positioned at or incorporated into the robot system 12. In addition, the system 10 may include one or more display screens 20 for displaying the visual representation of the cut procedure, and a navigation system 22 in communication with the tracking device 18 and the display screen 20. The navigation system 22 may include a computer 24 having a computer processing unit (CPU) 26 configured to perform one or more algorithms that compute and render the visual representation, and output the visual representation to the display screen 20 as described in further detail below. In some arrangements, the CPU 26 may include a graphics processing unit (GPU) 28 to assist the CPU 26 in performing the rendering calculations.

Figure 2:
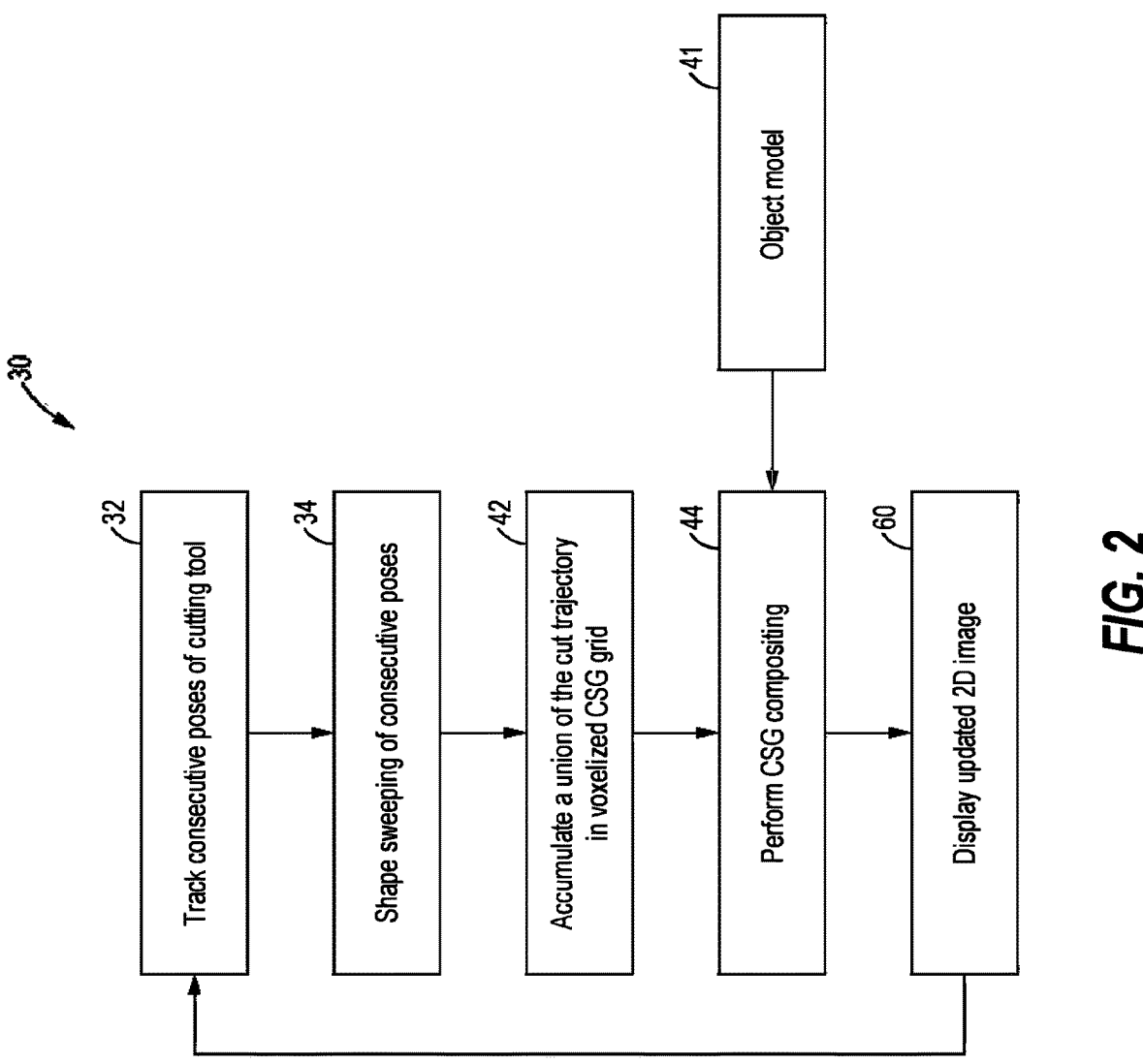
FIG. 2 is a flowchart of a series of steps involved in generating the visual representation of the cut procedure, in accordance with a method of the present disclosure.

Turning now to FIG. 2, a method 30 for generating the visual representation of the cut procedure as can be performed by the CPU 26 is shown. Further details of the steps of the method 30 are provided below with reference to FIGS. 8-9. At a first block 32, the consecutive poses of the cutting tool 16 as it follows its cutting trajectory during the cut procedure may be tracked based on input from the optical localization system. Each of the consecutive poses represents the discrete position/orientation of the cutting tool 16 at a particular point in time as captured by the optical localization system.

Figures 3, 4, 5, 6, 7:
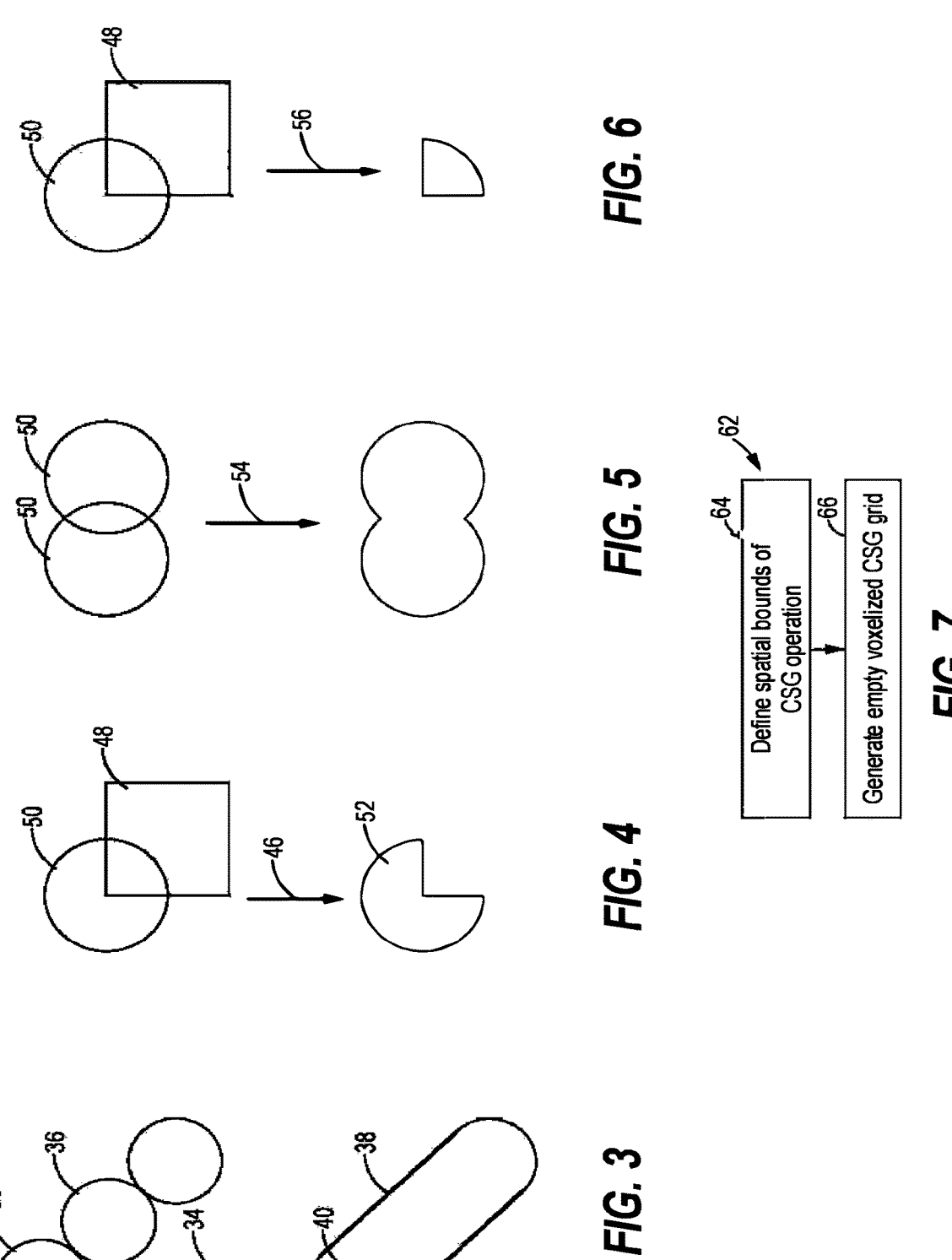
FIG. 3 is a schematic representation of the concept of shape sweeping of consecutive poses of the cutting tool, in accordance with the present disclosure.
FIG. 4 is a schematic representation of a CSG operation of subtraction, in accordance with the present disclosure.
FIG. 5 is a schematic representation of a CSG operation of union, in accordance with the present disclosure.
FIG. 6 is a schematic operation of a CSG operation of intersection, in accordance with the present disclosure.
FIG. 7 is a flowchart of steps involved in generating an empty voxelized constructive solid geometry (CSG) grid for accumulation of the union of the cut trajectory, in accordance with a method of the present disclosure.

Shape sweeping of the consecutive poses of the cutting tool 16 up to the particular point in time may be performed according to a block 34. The concept of the shape sweeping as performed during the block 34 is schematically depicted in FIG. 3. Although the cutting tool 16 may, in actuality, follow a smooth cutting path/trajectory during the cut procedure, the tracked consecutive poses 36 of the cutting tool 16 may be detected as discrete shapes due to sparse temporal sampling of the poses 36 by the tracking device 18. For instance, if the cutting tool 16 is a burr, the tracked consecutive poses 36 may be distinct spherical shapes, as shown in FIG. 3.

To correct for the temporal resolution of the tracking device 18 and provide a smoother visual output that more closely reflects the smooth cutting path followed by the cutting tool 16, shape sweeping 34 may be applied to the consecutive poses 36, as shown. The shape sweeping 34 may enclose the consecutive poses 36 in a smooth surface 38 to provide a smooth representation of a cut trajectory 40 followed by the cutting tool 16. The shape sweeping procedure provides a smoother visual representation of the cut object as explained further below with reference to FIG. 13.

In the example of FIG. 3, the shape sweeping 34 combines the spherical poses 36 into a capsule-like structure having the smooth surface 38. However, it is noted that shape sweeping as disclosed herein may be applied to a variety of cutting tools having different shapes and may be performed on any closed pose geometry such as, but not limited to, burr-ellipsoid/sphere, saw-rectangular cuboid, and reamer/half-sphere shapes. The swept shape may be generated in any suitable fashion, such as via piecewise linear or higher order (e.g., spline) approximation.

Turning back to FIG. 2, a union of the cut trajectory 40 may be accumulated in a three-dimensional voxelized constructive solid geometry (CSG) grid to produce an object space representation of the union of the cut trajectory 40 up to the particular point in time in the cut procedure (block 42). The voxelized CSG grid may be continuously updated with the union of cut trajectory as the cutting procedure progresses. That is, the voxelized CSG grid may be iteratively updated with the current cut trajectory as the position of the tool changes and removes more material from the object during the cut procedure (see below).

According to a next block 44, CSG compositing may be performed. In addition to other steps described further below with reference to FIG. 9, the CSG compositing step may involve performing a CSG operation on the object space representation of the union of the cut trajectory 40 and a three-dimensional model 41 of the object that is being cut. For example, if the object is bone, the three-dimensional model of the bone may be generated by segmenting a computerized tomography (CT) scan of the bone. If the object being cut is of a softer nature, e.g., flesh or a tumor, the three-dimensional model may change lightly between sequential renderings. The CSG operation may be performed using non-polygonal iso-surface ray marching as described further below with reference to FIG. 12.

In the context of a surgical bone resection procedure, for example, the CSG operation performed during the block 44 may be subtraction of the union of the cut trajectory 40 from the bone model to produce a 2D image of the resected bone. However, depending on the procedure that is performed on the object, other types of CSG operations may be performed such as union, intersection, and painting. Further descriptions of some of the types of CSG operations that may be performed during the block 44 are provided below.

In the CSG operation of subtraction (see FIG. 4), one object is subtracted from a primary object. The operation of subtraction produces a solid having a boundary that is made up of (a) all external points of the primary object that lie outside of the subtracted object, and (b) all external points of the subtracted object that lie inside the primary object. For example, the subtraction 46 of a cube 48 intersecting a quarter of a sphere 50 may be a three-quarter sphere 52 (see FIG. 4). In the CSG operation of union (see FIG. 5), an object is created that combines two or more base objects. Points that are on the boundary of one of the combined objects but are also located internal to other objects are not visible in the combined object. The union 54 of two spheres 50 is schematically depicted in FIG. 5. In the CSG operation of intersection, an object is created from base objects where the boundary is made up of all points that are both external to one object and internal to the other object. For example, FIG. 6 depicts the result of the intersection 56 of a sphere 50 with a cube 48.

Referring again to FIG. 2, upon completion of the block 44, the CPU 26 may output a 2D image of the result of the CSG operation to the display screen 20 (block 60). The 2D image may be continuously updated throughout the cut procedure by repeating the method 30 and continuously displaying the updated 2D image at the display screen 20. The method of FIG. 2 may be repeated with enough frequency so that the 2D image is updated in real time, or at least with enough frequency so that the user perceives the updates as occurring in real time (perceived real time).

Prior to accumulating the cut trajectory 40 in the voxelized CSG grid, an empty voxelized CSG grid may be generated according to the method 62 of FIG. 7. Beginning at a block 64, the spatial bounds of the CSG operation may be defined as the intersection of the bounding box (geometric surface) of the object that is cut and the bounding box of the allowed volume of the object that can be removed during the cut procedure. Optionally, a margin may be added to the intersection to allow cuts made outside of the allowed volume to be visualized at the display screen. Once the spatial bounds of the CSG operation has been defined by the block 64, the empty voxelized CSG grid is generated within the defined spatial bounds according to a block 66.

Figure 8:
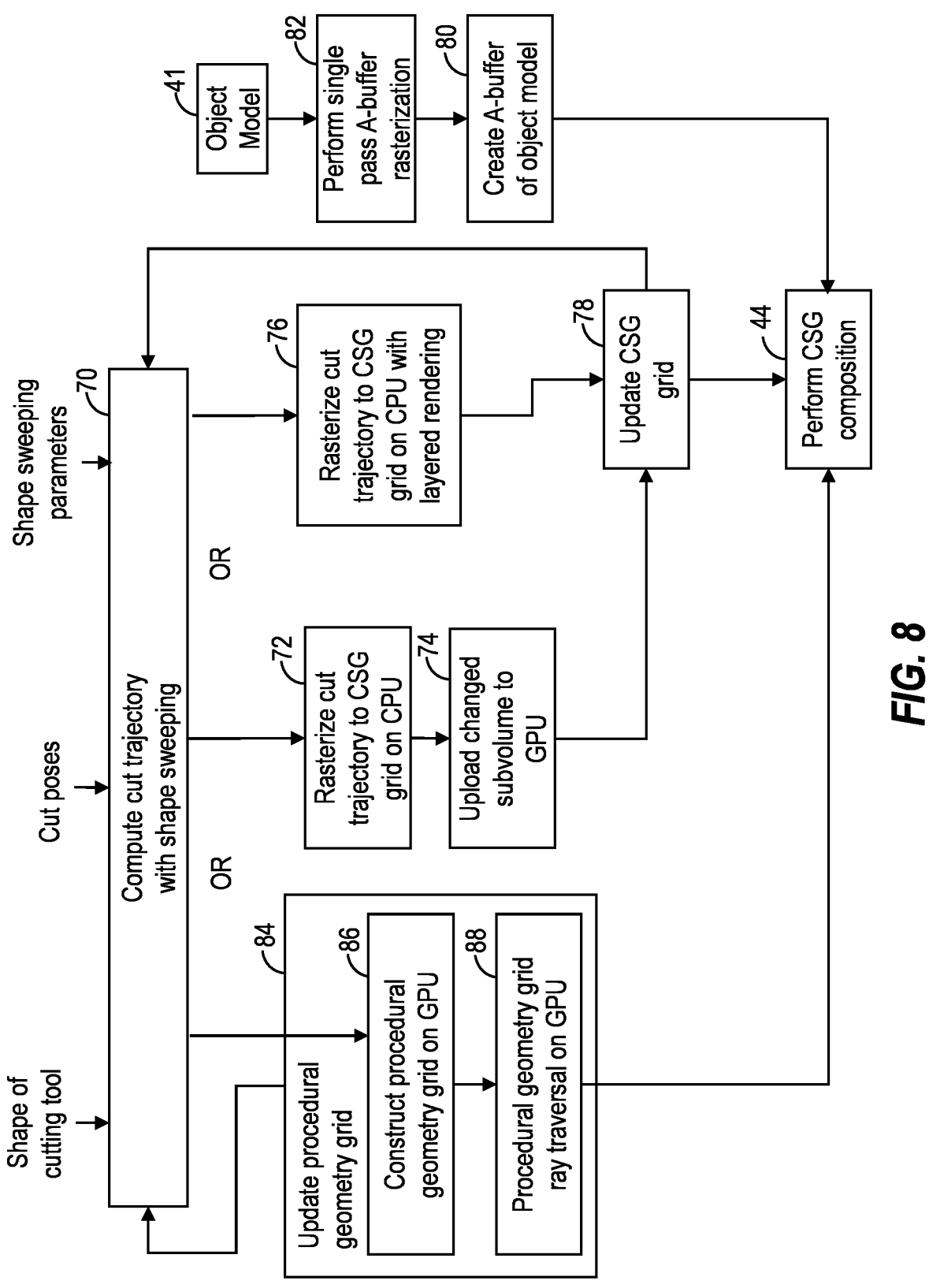
FIG. 8 is a flowchart of a series of steps that may be involved in the method of FIG. 2, in accordance of a method of the present disclosure.

Turning now to FIG. 8, steps that may be involved in the method 30 of FIG. 2 are schematically depicted. At a block 70, the cut trajectory 40 may be computed using shape sweeping 34 taking into account the shape of the cutting tool 16, the tracked consecutive poses 36, as well as the parameters for shape sweeping (also see FIG. 3). The cut trajectory 40 may then be rasterized into the voxelized CSG grid using the GPU 28 or a combination of the CPU 26 and the GPU 28. For instance, the rasterization may be performed on the CPU 26 according to a block 72, and only the sub-volume of the cut trajectory 40 that has changed since the last update may be transferred to the GPU 28 according to a block 74. Alternatively, the rasterization of the cut trajectory 40 may be performed on the GPU 28 according to a block 76. If performed on the GPU 28, the rasterization may be carried out with layered rendering (layer-by-layer rasterization) since the GPU 28 may only be capable of rendering 2D images. As such, one may decide to perform the rasterization by blocks 72 and 74, or by block 76, depending on which strategy is more efficient. FIG. 8 also shows an option of using a procedural geometry grid (block 84), described below.

Upon completion of rasterization of the cut trajectory 40, the voxelized CSG grid may be updated with the changed sub-volume of the cut trajectory 40 according to a next block 78. By continuously repeating the blocks 70, 72 and 74 (or 76), and 78 throughout the cut procedure, the union of the cut trajectory 40 may be iteratively updated in the voxelized CSG grid up to the current point in time of the cut procedure.

In addition, an A-buffer of the object model 41 may be created (block 80) by performing single-pass A-buffer rasterization on the object model 41 without a depth test (block 82). Single-pass A-buffer rasterization may reduce the cost of the rasterization as more passes increases the cost of the computation. The A-buffer may be a data structure describing the depth complexity of the object in image space from a viewpoint of a virtual camera. This A-buffer and the updated voxelized CSG grid may be used for the CSG compositing step (block 44) as described in further detail below.

Figure 21:
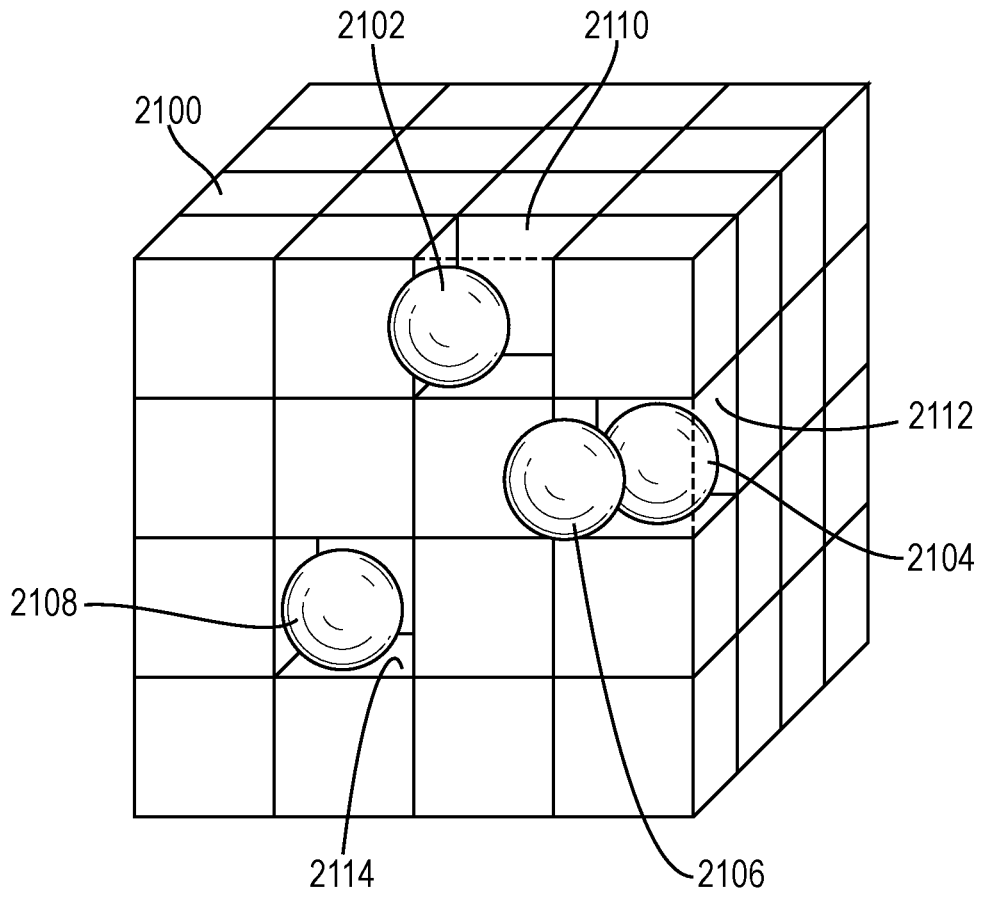
FIG. 21 is an illustration of use of procedural geometry, according to some embodiments.

In an embodiments where a procedural geometry grid is used (i.e., block 84 is executed), the cut trajectory accumulated with shape sweeping in block 70 is provided to block 84. Block 84 includes construction of a procedural geometry grid on the GPU 28 at block 86, followed by ray traversal of the procedural geometry grid on the GPU 28. As used herein, procedural geometry refers to a shape that is represented mathematically (e.g., general primitive), and can include, for example, a sphere, a capsule, a cylinder, a box, a plane, a cone, a wedge, etc. For example, a sphere can be represented mathematically by a center point and a radius (e.g., rather than a surface of tessellations or other approach). The procedural geometry grid refers to a three-dimensional bounding box (e.g., axis-aligned bounding box) divided into voxels, where each voxel is associated with a list (e.g., linked list) of procedural geometry. FIG. 21 shows an example illustration of a procedural geometry grid 2100 having associated procedural geometry, shown as a first sphere 2102, a second sphere 2104, third sphere 2106, and fourth sphere 2108. As shown, the first sphere 2102 is associated with a first voxel 2110, while the second sphere 2104 and third sphere 2106 are associated with a second voxel 2112, and the fourth sphere 2108 is associated with a third voxel 2114. Different numbers of different procedural geometries can occupy a voxel in various embodiments. This approach allows the mathematical ideal of such spheres and other shapes to be represented directly in the approach used for visualization in block 84. Further details of the is approach are described in FIGS. 22-23 below. Block 84 is thereby adapted to provide a grid that can be used in the CSG composition step of block 44, according to some embodiments.

Figure 9:
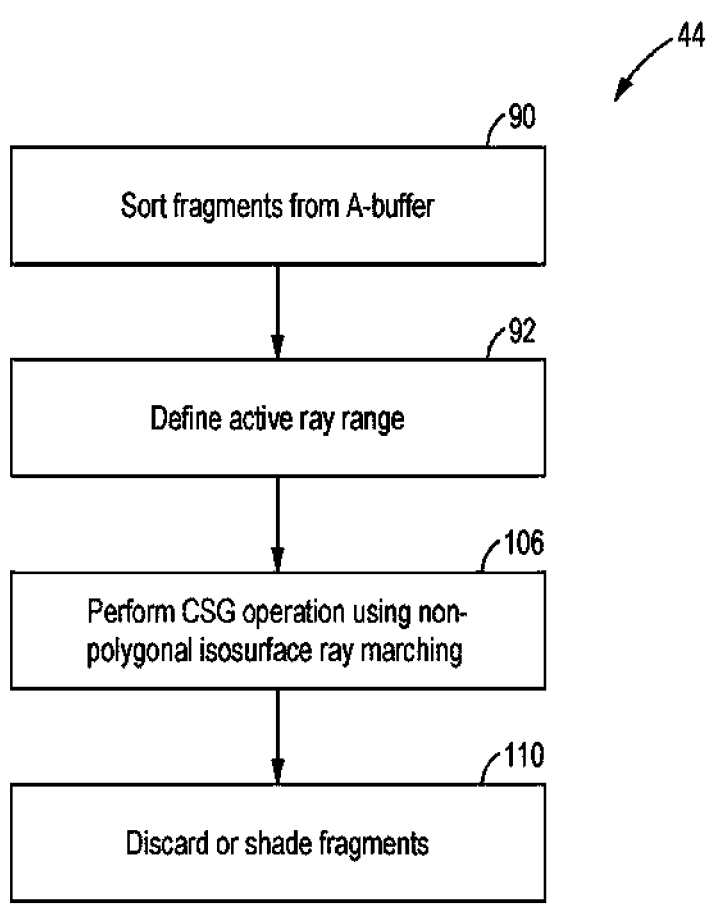
FIG. 9 is a flowchart of a series of steps that may be involved in performing CSG compositing, in accordance with the method of FIG. 2.

Turning now to FIG. 9, steps that may be involved in performing CSG compositing (block 44) are shown. At a first block 90, fragment sorting from the object model A-buffer may be performed. Specifically, the block 90 may involve reading the fragments from the A-buffer and sorting the fragments according to their depths.

Figure 10:
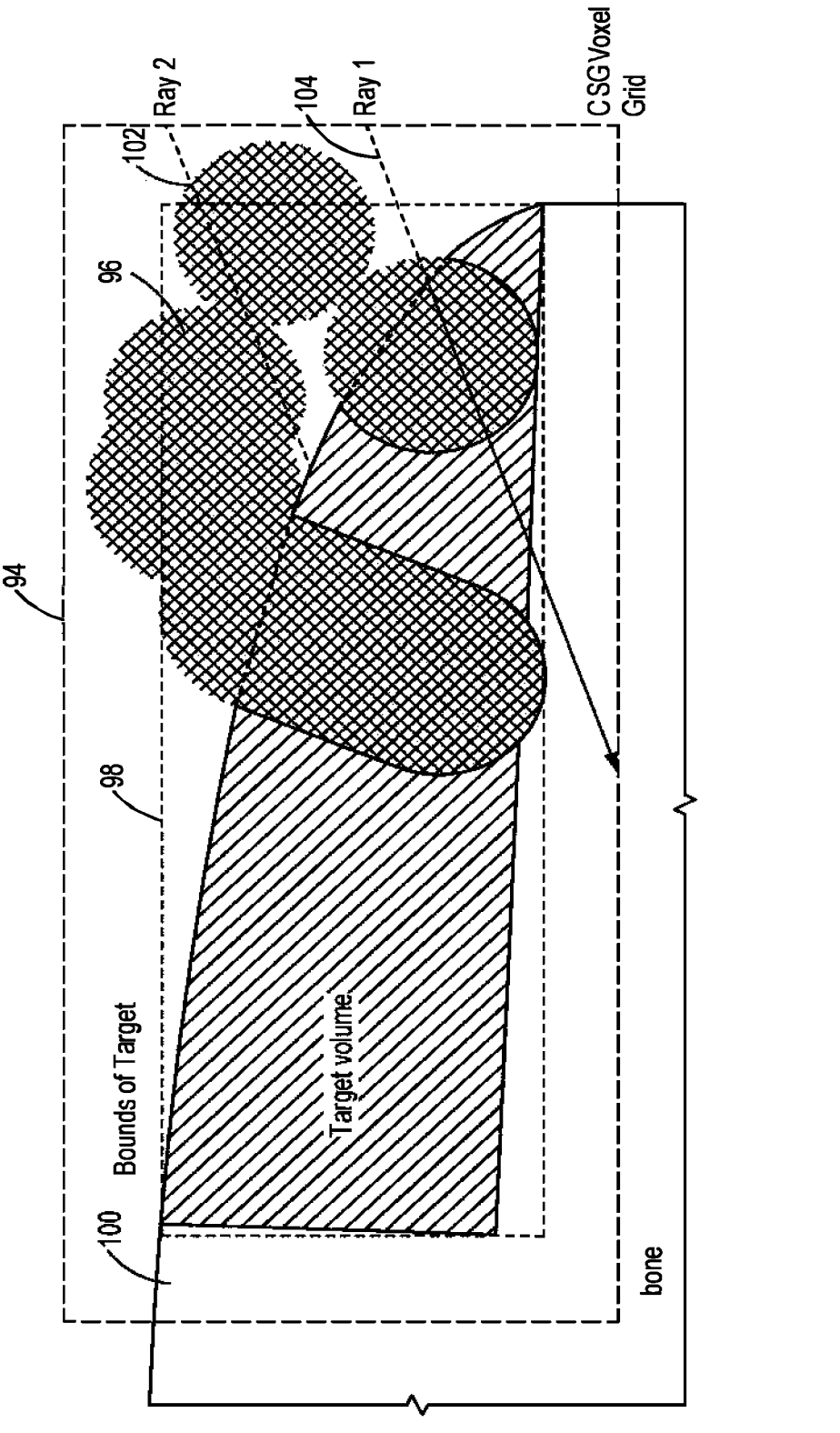
FIG. 10 is a schematic representation of the concept of defining an active ray range for non-polygonal iso-surface ray marching, in accordance with a method of the present disclosure.

At a block 92, the active ray range for non-polygonal iso-surface ray marching may be defined to reduce the active ray range for the ray marching and increase the efficiency of the computation. A schematic illustration of defining the active ray range as performed during the block 92 is shown in FIG. 10. FIG. 10 shows the voxelized CSG grid 94, the union of the cut trajectory 96, and a bounding box 98 of the allowed volume of the object 100 (e.g., bone) that is allowed to be cut during the cut procedure. In non-polygonal iso-surface ray marching, a plurality of rays (e.g., rays 102 and 104) from a particular viewpoint of a virtual camera may be cast or marched through the voxelized CSG grid 94 to iteratively search for intersection points. The intersection points may be used to produce an image space (2D) surface representation of the cut procedure that is displayed at the display screen 20. Each of the rays 102 and 104 may correspond to a pixel in the 2D image that is produced. Defining the active ray range according to the block 92 restricts the search for ray marching and increases the efficiency of the CSG operation. More particularly, according to the block 92, ray marching may be skipped (or "inactive") if the bounding box 98 of the object 100 and the voxelized CSG grid 94 do not overlap along the ray (see dashed sections of exemplary rays 102 and 104 corresponding to the "inactive" ray range). In the "inactive" ray range, no computation is performed. Otherwise, the rays are iterated in the "active" ray range as shown by the solid section of the ray 104. In the "active" ray range, the start of the marching is either the closest surface of the object 100 (from the A-buffer) or where the ray enters the voxelized CSG grid 94, whichever is farther (equation 1). The ray marching is terminated at the furthest intersection of the ray and the object 100 (from the A-buffer), or if CSG grid 94 is exited, whichever happens earlier (equation 2). For example, in FIG. 10, the dashed sections of the exemplary rays 102 and 104 are skipped during marching because they lie outside of the object 100, with ray 102 being terminated as soon as the object 100 is reached since at that point the CSG grid 94 is not set.

$$t_{start} = \max(t_{object\_closest}, t_{grid\_entry}) \qquad \text{(equation 1)}$$

$$t_{end} = \min(t_{grid\_exit}, t_{object\_furthest}) \qquad \text{(equation 2)}$$

Figure 11:
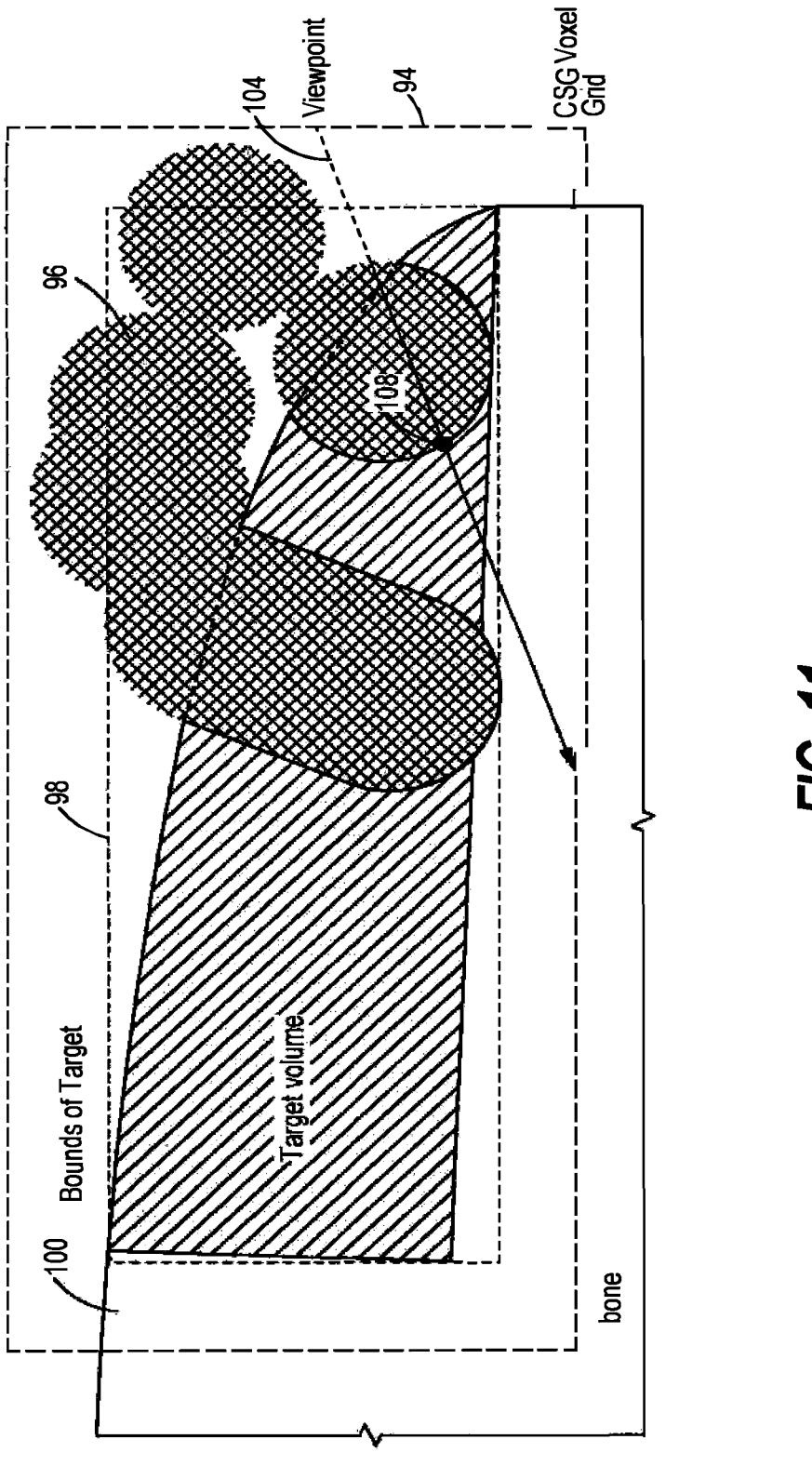
FIG. 11 is a schematic representation of non-polygonal iso-surface ray marching to compute a subtraction of the union of the cut trajectory from the object, in accordance with a method of the present disclosure.

With the active ray range defined as described above, the CSG operation may be performed on the object 100 (from A-buffer) and the union of the cut trajectory 96 using non-polygonal iso-surface ray marching (block 106). It will be appreciated that other CSG operations may be implemented, e.g., surface painting, intersection, etc. FIG. 11 depicts an example of using non-polygonal iso-surface ray marching to display the results of subtracting the union of the cut trajectory 96 from the object 100. For each pixel, a ray 104 is marched through the active ray range (solid portion of the ray 104) from a viewpoint of the virtual camera, and the intersection point 108 is determined as the closest intersection point that is inside the object 100 and outside of the union of the cut trajectory 96. The intersection point 108 represents the cut surface of the object 100, and is used to produce the 2D surface representation that is displayed at the display screen 20.

If the object 100 and the union of the cut trajectory 96 do not overlap along a ray (indicating that the object has not been cut at that location), the object surface is displayed as uncut in the 2D image. Iteratively searching the voxelized CSG grid 94 for intersection points in this manner produces the 2D surface representation of the object as it is cut during the cut procedure. For example, in the context of bone resection, the block 106 may result in a 2D surface representation of the resected bone surface.

Referring again to FIG. 9, the CSG compositing block 44 may further include discarding or shading fragments of the 2D surface representation produced from the CSG operation to refine the 2D image (block 110). In particular, during the block 110, a machining calculation may be applied that determines the shading of each fragment and determines the red, green, and blue color contribution of the fragments at each pixel. In the context of surgical bone resection procedures, regions of bone that are to be resected may be colored in green, and regions where the cutting tool 16 has penetrated beyond the planned region may be colored in red. The block 110 may further involve discarding the fragments that are not visible. The refined 2D image may be displayed at the display screen 20 (block 60, FIG. 2).

In a further embodiment, a display of the total removed material, total material remaining to be removed, or both may be generated for the user's guidance. For example, the display may indicate that 80% of the material to be removed has been removed, and 20% of the material to be removed remains on the object.

Figures 12, 13:
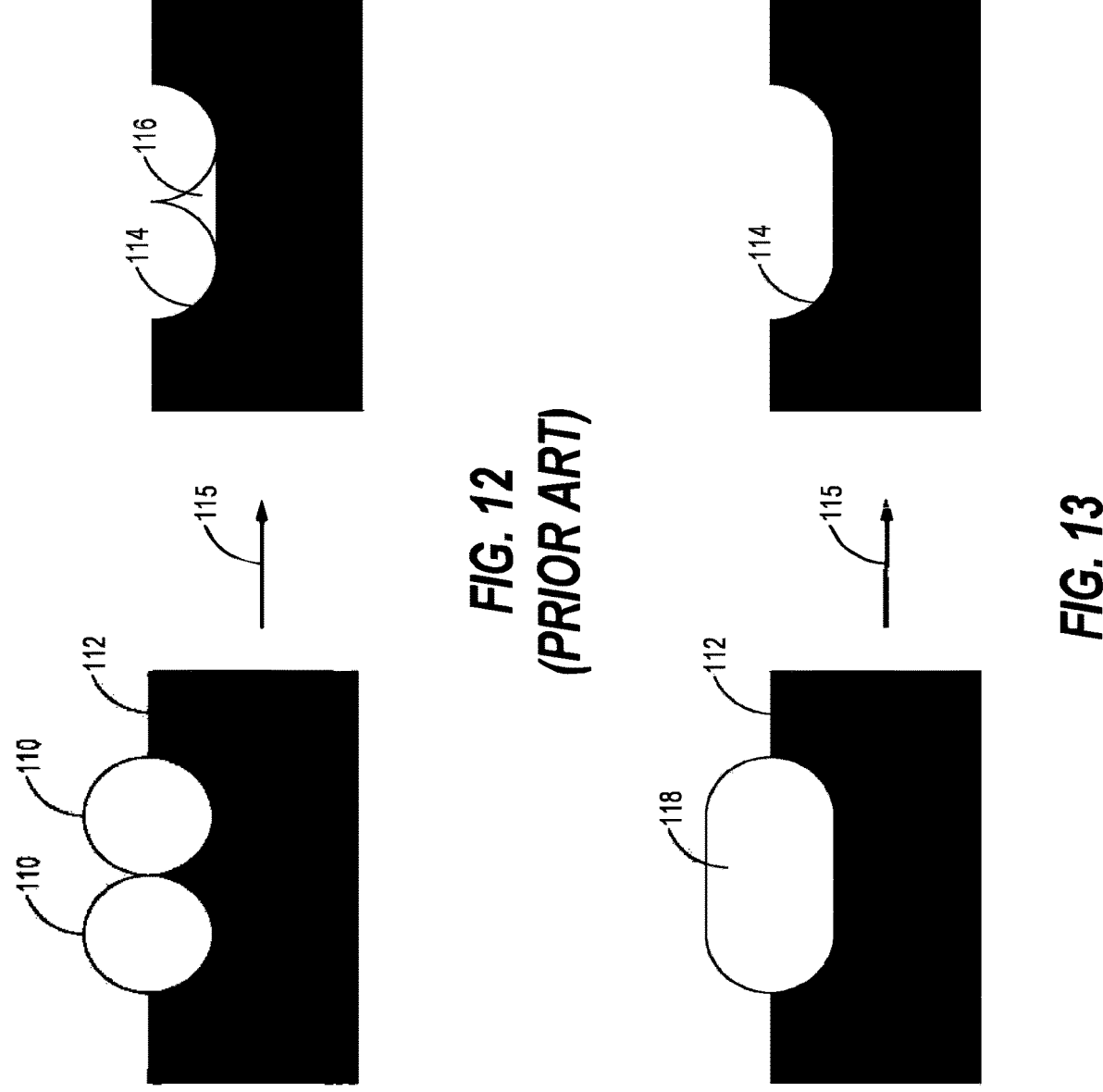
FIG. 12 is schematic representation of subtracting an un-swept cut trajectory from the object, in accordance with the prior art.
FIG. 13 is a schematic representation of subtracting a swept cut trajectory from the object to produce smooth cut surfaces in the visual representation, in accordance with the present disclosure.

The present application applies shape sweeping 34 to produce a smoother visual representation of the cut procedure. FIG. 12 shows an object surface 114 produced after subtracting un-swept cut poses 110 from an object model 112 in accordance with the prior art. As can be seen, due to the temporal resolution of the tracking method used to track the poses of the cutting tool 16, the poses 110 may be detected as discrete shapes representing the shape of the cutting tool 16. As a result, the displayed object surface 114 after subtraction 115 of the un-swept cut poses 110 may have edgy, wave-like ridges 116 as artifacts of the sparse temporal sampling of the cut poses 110. In contrast, the subtraction of swept cut poses 118 from the object model 112 in accordance with the present disclosure avoids the leftover ridges and produces a smoother visual representation of the cut object surface 114.

In general, it can therefore be seen that the technology disclosed herein may find applicability in a variety of settings such as, but not limited to, surgery and machining. More specifically, the present disclosure may be applicable in various applications that may benefit from real time visualization of the progress of material removal from an object during a manual or automated cut procedure. Although robotic bone resection is given as one example, the technology disclosed herein may also be applicable to manual surgery, such as manual bone resection, to cutting or milling operations, as well as other types of operations.

Current methods used to produce a visual representation of bone resection procedures may be computationally expensive due to the large number of tool positions that need to be subtracted from the bone mod The computational cost of current methods that rely on depth peeling may increase with increasing depth complexity of the scene. Moreover, the results of the computation may be invalidated and require re-computation if the virtual camera is moved or rotated.

By contrast, the approach discussed above has a constant computational cost with respect to the depth complexity of the scene. The computation of the union of the cut trajectory as disclosed herein happens incrementally at a constant computational cost by rasterizing the model of the cut trajectory to a voxelized CSG grid that (spatially) covers the planned resection volume (with an optional margin). Creating the image-space fragments that describe the voxelized model in a pixel also happens at the constant computational cost of marching rays through the voxelized CSG grid. The resolution of the voxelized CSG grid determines the computational cost, and is fixed beforehand. The voxelized CSG representation also removes the burden of processing overlapping or duplicate positions. Furthermore, high visual quality of resected surfaces is achieved by sub-voxel accurate filtering during non-polygonal iso-surface ray marching. The initial iso-surface intersections are refined in a binary search manner by reducing the marching step size.

As disclosed herein, the voxelized CSG representation may be rasterized on the CPU or on the GPU by layered rendering of the CSG grid into slices, depending on which rasterization strategy is more efficient. If the rasterization happens on the CPU, only the sub-volume of the cut trajectory that has changed since the last update is uploaded to the GPU to further enhance efficiency. This sub-volume is defined by the bounding box of the updated cut pose of the cut trajectory.

The present disclosure also offers another improvement to the quality of the visual representation over existing methods. In current technologies, the consecutive poses of the cutting tool may be too far apart due to sparse temporal sampling of the tool position tracking device, resulting in leftover ridges in the displayed image that may not accurately reflect the smooth cutting path followed by the cutting tool. The present disclosure applies shape sweeping to represent the consecutive poses within a smooth enclosing surface to prevent ridge artifacts from appearing in the visual representation of the cut procedure. Advantageously, this results in visually smoother resected surfaces in the displayed image which may more closely represent the true appearance of the resected object.

Further technical advantages can be achieved by additionally or alternatively applying the features described below with reference to FIGS. 14-19. As described in detail below, computational expense can be further reduced by orienting a graphics coordinate system (e.g., voxel grid, voxelized CSG grid 94) and/or bounding a volume for visualization calculations (e.g., defining bounding box 98) based on a cutting plan (e.g., surgical plan), for example by reducing the total volume for rasterization and CSG operations while capturing the areas of interest for the user. Such an approach can also reduce visualization artifacts, for example by aligning a voxel grid (e.g., voxelized CSG grid 94) with the planned cut such that successfully performing the planned cut results in a surface which is inherently smooth in the aligned voxel gird. Thus, as will be apparent from the following description, technical improvements in graphical visualization technologies specifically adapted for the technical field of surgical navigation and guidance and analogous applications are provided by the features shown in 14-19 and detailed below.

Referring now to FIG. 14, a flowchart of a process 1400 is shown, according to some embodiments. Process 1400 can be executed by surgical system, for example a robotic surgery system, surgical navigation system, etc. in various embodiments. For example, in some embodiments, process 1400 can be executed by the system 10, for example by or using the navigation system 22 (e.g., by the CPU 26). The process 1400 can optionally be executed in combination with method 30 and/or method 62 described above, in some embodiments. The discussion of FIG. 14 refers to FIG. 15 for sake of example, which shows an illustration of a bone model 1500, planned bone modification plane 1502, and bounding box 1504, according to some embodiments.

Figure 15:
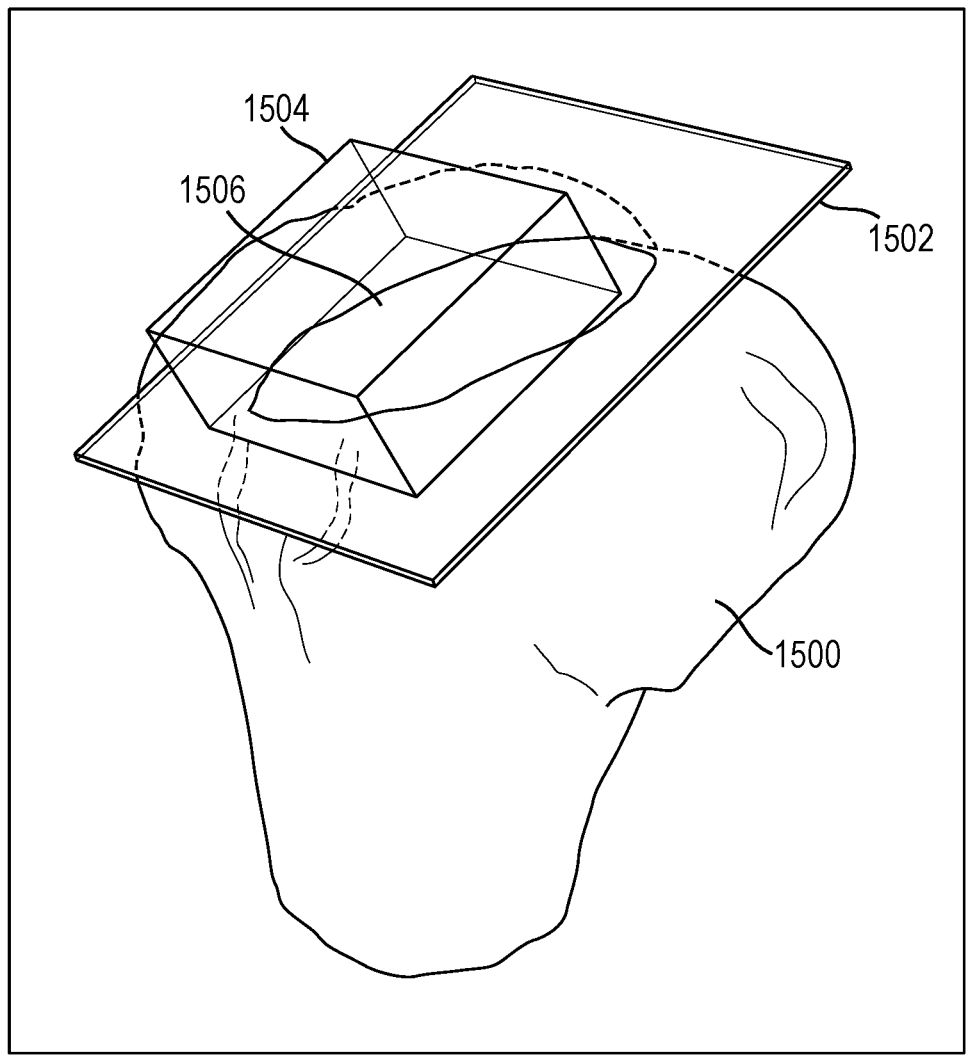
FIG. 15 is an illustration of a bone model, cut plane, and bounding box as used in some examples of the plan-dependent visualization process of FIG. 14, according to some embodiments.

At step 1402, a bone model is provided. The bone model is a three-dimensional virtual representation of a bone. For example, in some embodiments the bone model is generated from segmented CT images (or other types of medical imaging) of a patient's bone. In some embodiments, the bone model is a generic (standard, non-patient-specific) model of a bone. As one example, FIG. 15 shows a bone model 1500 of femur.

At step 1404, a surgical plan is provided which indicates a plan (planned cut, cut plan, planned bone modification) for a bone modification (cut, burr, drill, sculpt, etc.) relative to the bone model. The surgical plan can also indicate one or more additional bone modifications (additional planned cuts), for example a sequence of bone modifications planned to prepare a surface of a bone to receive an implant. In some embodiments, step 1404 includes automatically generating the surgical plan based on patient characteristics and/or providing a graphical user interface that allows the user to adjust the surgical plan (e.g., by adjust a planned implant position relative to the bone model). In some examples, the planned cut indicated by the surgical plan is a plane (or is planar) and is defined relative to the bone model. For example, a plane having an orientation and position relative to a position and orientation of the bone model can be provided in step 1404. As one example, FIG. 15 shows a planned bone modification plane 1502 positioned and oriented relative to the bone model 1500.

At step 1406, a voxel grid (e.g., voxelized CSG grid 94) or other graphics coordinate system is oriented relative to the bone model based on the planned bone modification. Orienting a graphics coordinate system can be performed in step 1406 such that the planned bone modification has a constant value in one dimension of a three-dimensional graphics coordinate system. For example, where the planned bone modification is planar, step 1406 can include aligning the voxel grid to the planed bone modification such that a first dimension of the voxel grid is perpendicular to the planned bone modification, a second dimension of the voxel grid is parallel to the planned bone modification, and a third dimension of the voxel grid is parallel to the planned bone modification. In the example of FIG. 15, step 1406 includes orienting the voxel grid based on the planned bone modification plane 1502 such that the voxel grid (which itself has orthogonal dimensions, e.g., cubical voxels in the example of FIG. 15) has two coordinate dimensions parallel to the planned bone modification plane 1502 and one coordinate dimension perpendicular to the planned bone modification plane 1502, i.e., such that the planned bone modification plane 1502 is constantly-valued in one dimension of the voxel grid and extends in all directions in the other two dimensions of the voxel grid.

Orienting the voxel grid or other graphics coordinate system relative to the bone model in step 1406 can also be characterized as orienting the bone model relative to the voxel grid. Coordinate transformations can be used to translate between the voxel grid aligned to the planned bone modification and other coordinate systems used in a navigation or control process (e.g., used by system 10) (e.g., used by a tracking system, used for robotic control, etc.).

At step 1408, a bounding box is defined based on the planned bone modification and the voxel grid (or other graphics coordinate system). The bounding box can be a cube or rectangular box defined square to the voxel grid (e.g., with each surface of the bounding box being planar and having a constant value in a dimension of the graphics coordinate system), which can simplify calculations as compared to defining the bounding box in some other manner. Step 1408 can include spatially positioning the bounding box with one surface at or slightly to a first side of the planned bone modification (e.g., by one millimeter, two millimeters, three millimeters, etc.) with a remainder of bounding box to a second, opposing side of the planned bone modification. Step 1408 can also include sizing the bounding box such that all portions of the bone model on the second side of the planned bone modification (i.e., the portion(s) planned for resection) are enclosed in the bounding box, and, in some embodiments, limiting the extent of the bounding box to the extremities of such portions of the bone model in each coordinate dimension (e.g., with a slight offset).

FIG. 15 illustrates an example where the bounding box 1504 is positioned at the planned bone modification plane 1502 and sized to enclose a portion 1506 of the bone model 1500 planned for resection (i.e., portions separated from the remainder of the bone model 1500 by the planned bone modification plane 1502. The bounding box 1504 is thereby narrowly scoped to include the portions of the bone model

1500 intended to be affected during execution of the surgical plan to make the planned bone modification without encompassing substantial portions of the bone model not intended to be affected by the planned bone modification. Volume of the bounding box 1504 can thus be minimized while capturing all areas of interest to a user for visualization. The bounding box 1504 defined in step 1408 based on the planned bone modification and voxel grid is thereby limited to minimize the amount of rasterization, CSG calculations, ray casting, and/or other calculations required for generating visualizations, thus reducing computational expense and improving computational efficiency.

At step 1410, a real-time visualization of execution of the planned bone modification is generated using the bone model, the voxel grid, and, in some embodiments, data (e.g., from a tracking system) indicative of positions of a tool used to make the planned bone modification. In some embodiments, step 1410 includes determining voxels of the voxel grid shared by bone model and by an accumulation (e.g., sweep) of the tool positions (e.g., using a CSG operation as described above), and updating the visualization to remove (or color, shade, make transparent, etc.) the visualization of such voxels. Step 1410 can include generating a representation of a surface of the bone model resulting from removal of virtual bone from the voxels shared by the bone model and the accumulation of the tool positions. Step 1410 can be executed using the approaches described above with reference to FIGS. 1-13, for example.

Figure 16:
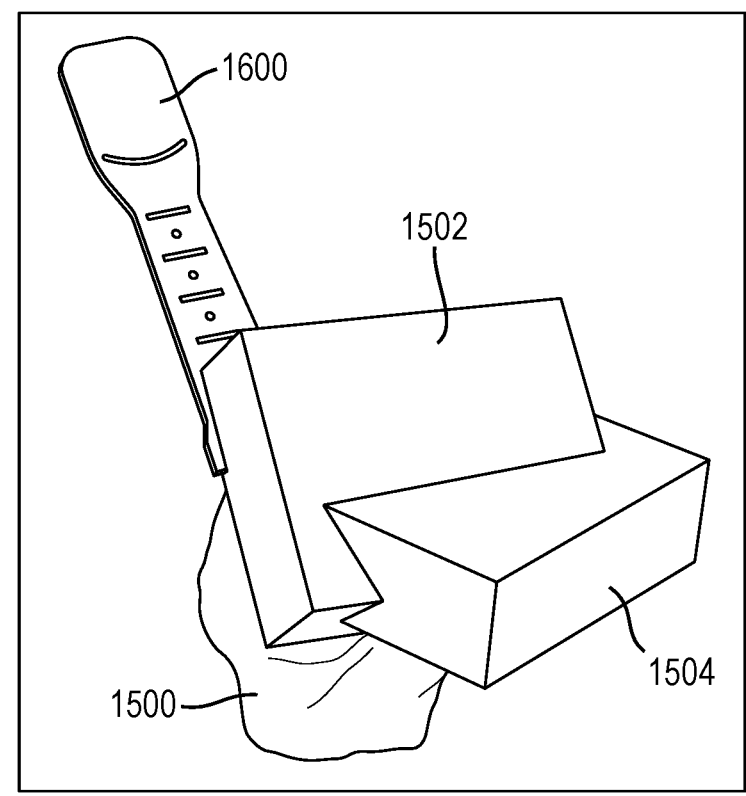
FIG. 16 is a schematic illustration relating to the plan-dependent visualization process of FIG. 14, according to some embodiments.
Figure 17:
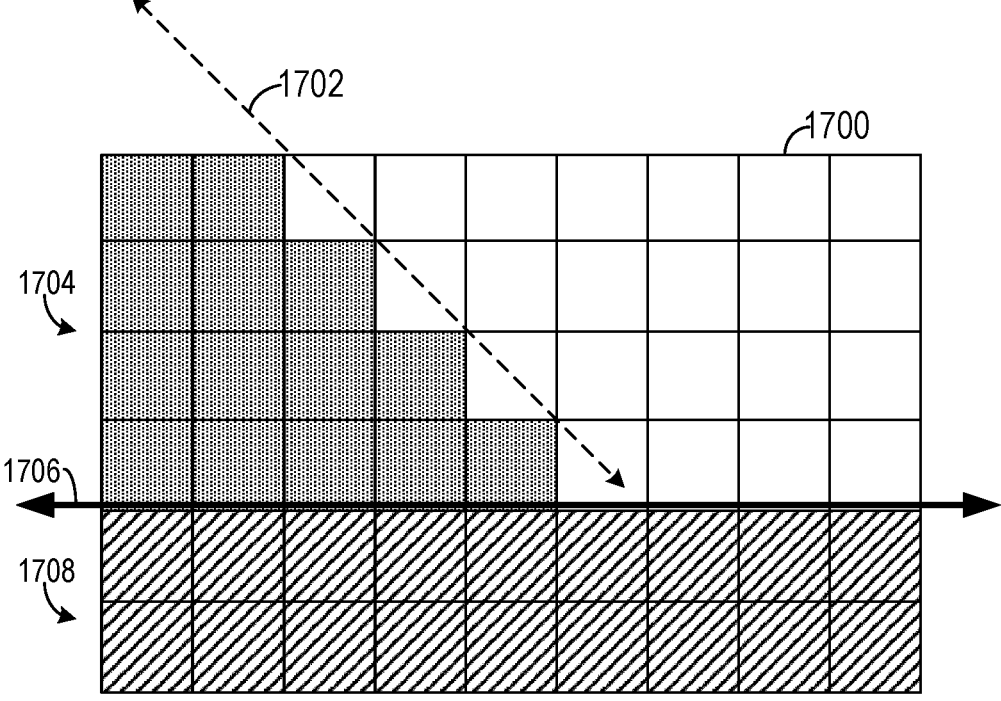
FIG. 17 is another schematic illustration relating to the plan-dependent visualization process of FIG. 14, according to some embodiments.

Due to alignment of the planned bone modification with the voxel grid (or other graphics coordinate system), the visualizations generated in step 1410 in inherently-smooth surfaces when the bone modification is executed according to plan. FIGS. 16-17 include schematic diagrams illustrative of such effects. FIG. 16 illustrates a cutting tool 1600 relative to a bone model 1500 along with a plan-aligned box 1602 and a bone-axis-aligned box 1604. The plan-aligned box 1602 illustrates the orientation of a voxel grid arranged relative to the bone model 1500 according to the steps of process 1400, while the bone-axis-aligned box 1604 illustrates a voxel grid aligned to the bone model 1500 agnostic to the planned bone modification. As shown in FIG. 16, a surgeon following the surgical plan will operate the cutting tool 1600 along a direction parallel to a surface of the plan-aligned box 1602 (e.g., along a coordinate direction of the voxel grid), i.e., the cutting tool 1600 aligned to the plan and thus the box 1602 as intended. Such alignment and parallel movements can simplify calculations and reduce visualization artifacts. In contrast, the surgical tool 1600 is shown at an angle relative to all surfaces and coordinate directions of the bone-axis-aligned box 1604, which can lead to visualization artifacts such as steps between voxels as shown in FIG. 17.

FIG. 17 illustrates a grid 1700 (shown in two dimensions for the sake of explanation, with the principles illustrated extendable to three or more dimensions). As shown in FIG. 17, a first line 1702 extends across the grid 1700 in a direction non-parallel to either (any) coordinate dimension of the grid 1700. FIG. 17 also shows the boxes 1704 (voxels) of the grid 1700 beneath the first line 1702 as shaded/dotted. Because the first line 1702 is at an angle relative to the grid 1700, the boxes 1704 beneath the first line 1702 form steps (ridges, jumps, artifacts, etc.). A visualization generated using the boxes 1704 will thus include visualization artifacts, i.e., the steps, thus inaccurately representing the straight line 1702.

FIG. 17 also shows a second line 1706 aligned with the grid 1700. The second line 1706 can be aligned with the grid 1700 as result of orienting the grid 1700 based on a surgical plan as in process 1400. Because the second line 1704 is aligned with the grid 1700, boxes 1708 under the second line 1706 can be highlighted without steps, jumps, discontinuities, etc. A visualization generated of the boxes 1708 thus accurately represents the smooth, linear contour of the second line 1706 without visualization artifacts. In the context of process 1400, line 1704 can correspond to the positions of a tool as the planned bone modification is executed according to the surgical plan. Visualization based on tracking data as the tool moves along such a line (surface, etc.) can thus inherently result in no or limited visualization artifacts, as an effect of aligning the voxel grid based on the surgical plan in step 1406.

In some such embodiments, no or limited post-processing (e.g., smoothing, interpolation, etc.) is required to achieve a smooth appearance of the visualization, such that the visualization more closely corresponds to underlying data (e.g., tracking data) as compared to an approach where some post-processing approach is applied to hide the steps between boxes 1704. Computation efficiency can also be improved by minimizing the need for such post-processing.

Figure 18:
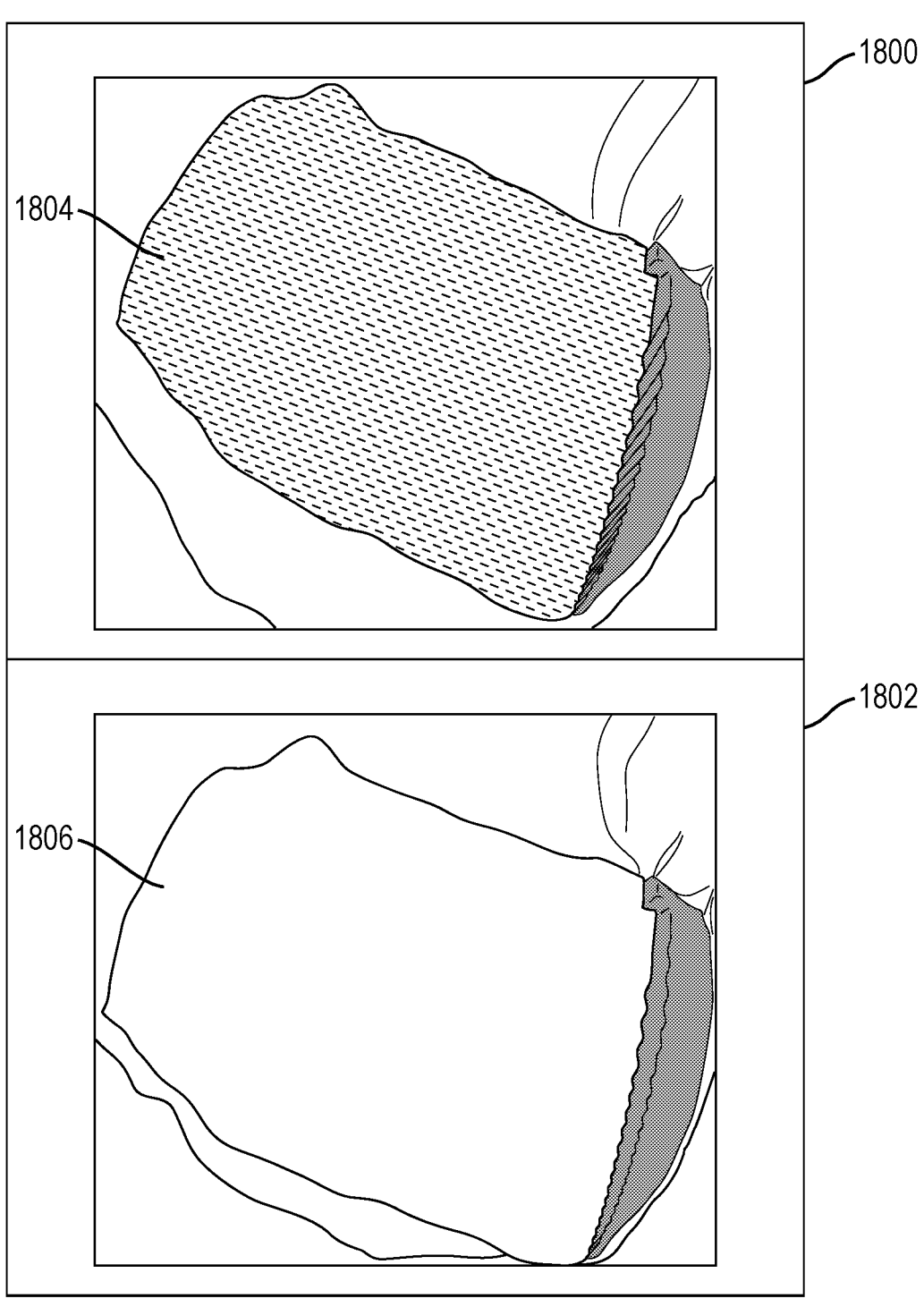
FIG. 18 is an illustration showing results of applying the plan-dependent visualization process of FIG. 14 as compared to another approach, according to experimental results in some embodiments.

FIG. 18 shows example visualizations, according to experimental results. In particular, FIG. 18 includes a first illustration 1800 generated without alignment of the voxel grid to the planned bone modification and a second illustration 1802 generated following process 1400 (e.g., including alignment of the voxel grid to the planned bone modification). The first illustrations 1800 includes visualization artifacts caused by misalignment to the voxel grid causing the appearance of a rough surface 1804. The second illustration 1802 is free of such visualization artifacts due to alignment of the voxel grid to a smooth surface 1806 resulting from a bone modification. FIG. 18 thereby provides experimental results showing improvements in visualization quality resulting from the techniques described herein, including by execution of process 1400.

Referring again FIG. 14, FIG. 14 illustrates that the process 1400 can return from step 1410 to step 1406. In particular, for procedures involving multiple planned bone modifications (e.g., multiple cuts at different angles to prepare a femur to receive an implant), process 1400 can include re-orienting the voxel grid based on an additional (subsequent, second, etc.) planned bone modification in response to an indication that a first (preceding, etc.) planned bone modification is completed (e.g., based on a user input, based on detecting from tracking data that a tool completed a full extent of the planned cut, etc.). Re-orienting the voxel can include changing the voxel grid from being aligned with the first planned bone modification to being aligned with the additional planned bone modification (e.g., so that a first dimension of the voxel grid becomes perpendicular to the additional planned bone modification while second and third dimensions of the voxel grid are parallel to the additional planned bone modification). The voxel grid is thus updated (re-oriented, moved, changed, rotated, etc.) for different stages of a surgical procedure (e.g., different cuts, different bone modifications, different subparts of a continuous bone modification, etc.) in order to provide efficient, artifact-free visualizations for multiple stages of a surgical procedure.

Figure 19:
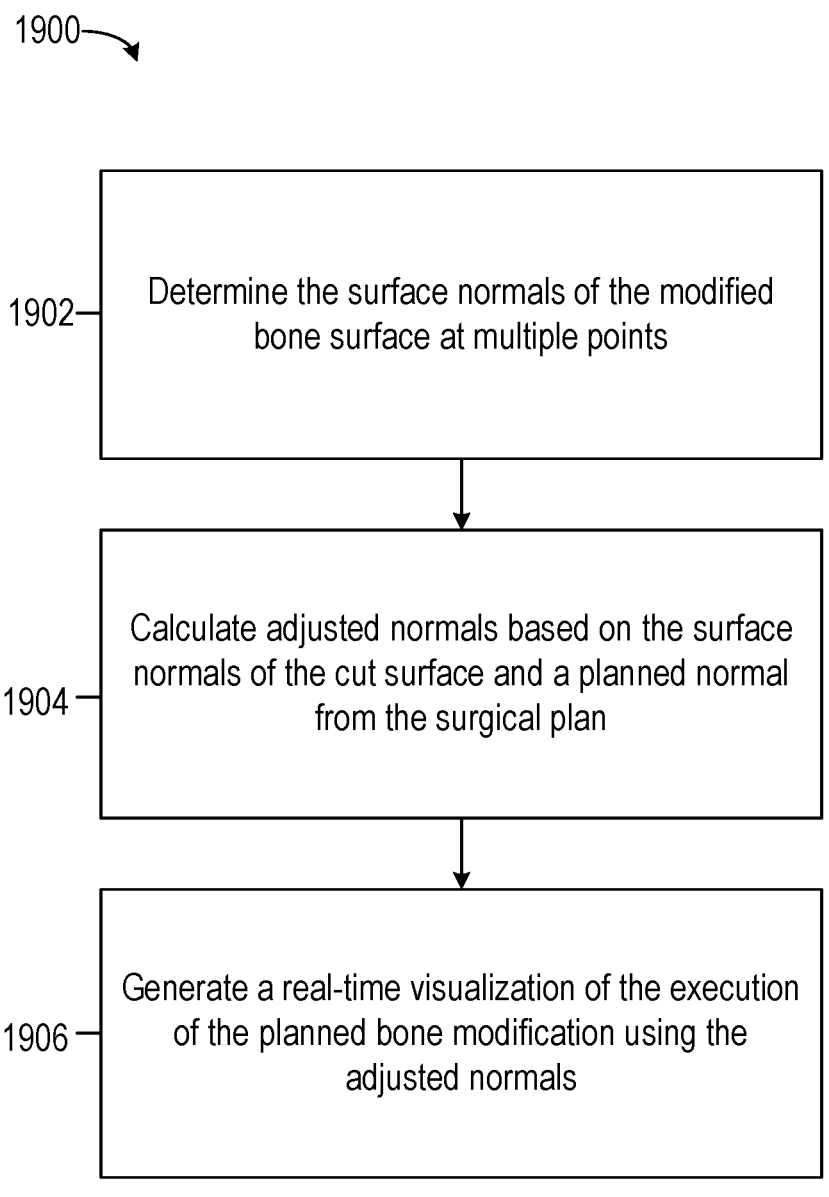
FIG. 19 is a flowchart of another plan-dependent visualization process, according to some embodiments.

Referring now to FIG. 19, a flowchart of a process 1900 providing a plan-dependent visualization feature is shown, according to some embodiments. Process 1900 can be used with process 1400 in some embodiments, for example as part of generating a real-time visualization of execution of the planned bone modification using the bone model and tool positions as in step 1410 of FIG. 14. Process 1900 may also be used in an implementation which omits some or all of process 1400. Process 1900 can be executed by execution by one or more processors of instructions stored in non-transitory computer-readable media, e.g., by the system 10 for example by or using the navigation system 22 (e.g., by the CPU 26). Process 1900 can advantageously use the surgical plan to eliminate visualization artifacts from the bone surface.

At step 1902, the surface normal of the modified bone surface is determined at multiple points. The multiple points may be points for which the intersection point 108 is within a threshold vicinity of the planned bone modification (e.g., planned cut plane). For example, the points used in step 1902 may be selected as the points for which $\|n_{plan}(p-o_{plan})\| < \epsilon$, where p is the location of the intersection point 108, $n_{plan}$ is the normal vector of the planned bone modification (e.g., planned resection plane), and $o_{plan}$ is the origin point of the planned bone modification (e.g., planned resection plane), and $\epsilon$ is a fixed threshold value, for example selected based on an expected amount of deviation in a cut, tolerance in a cutting workflow, etc., For such points, a normal of the surface of bone modification (e.g., actual resection surface) can be determined, for example by using a volume gradient approach applied to the voxel representation of the bone remaining after the CSG operations described herein. The normal of the surface of the bone modification calculated from the voxel representation for a given point is denoted here as $n_{grid}$.

At step 1904, adjusted normals are calculated based on $n_{plan}$ (the normal vector of the planned bone modification) and $n_{grid}$ (the normal of the modified bone surface as calculated from the voxel grid representation). The adjustment may be an interpolation between the two normal. In some embodiments, an adjusted normal $n_{adjusted}$ is calculated as $n_{adjusted} = (n_{grid} * \alpha) + (n_{plan} * (1-\alpha))$, where a is weighting parameter. In some embodiments, $\alpha$ has a value between 0.7 and 0.9, for example approximately 0.85. In some embodiments, $\alpha$ is a fixed value. In some embodiments, $\alpha$ is a function of the distance from the intersection point 108 to the planned bone modification.

To apply the normal modification when the resection involves multiple resection planes, some embodiments of process 1900 including keeping track of the associated resection plane during ray-casting of the raster volume. Since each raster volume may have a unique resection plane associated with it, information identifying the corresponding planned surface can be stored with (added to, tagged onto, etc.) intersection point 108. During the CSG subtraction step as described above, this information is used in some embodiments to identify which $n_{plan}$ and $o_{plan}$ are used in instances of steps 1902 and 1904.

At step 1906, a real-time visualization of the execution of the planned bone modification is generated using the adjusted normals (i.e., using $n_{adjusted}$ for different points). The adjusted normal can be used in surface shading approach, for example using Phong shading to generate the visualization. Use of the adjusted normals in step 1906 can reduce or eliminate artifacts which appear on the modified bone surface, such that the surface appears flat, smooth, etc. as displayed to a user.

Figure 20:
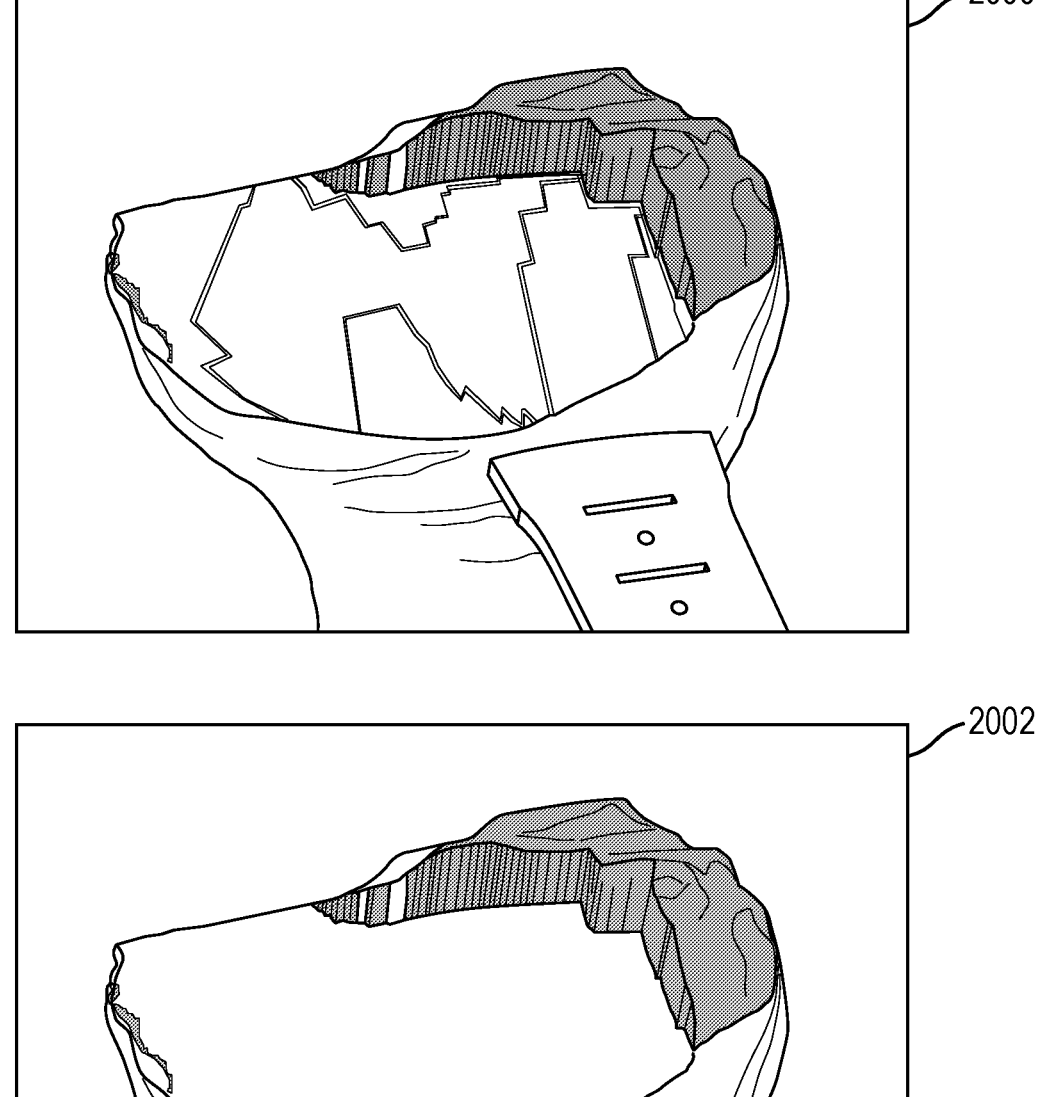
FIG. 20 is an illustration showing results of applying the plan-dependent visualization process of FIG. 19, according to some embodiments.

FIG. 20 shows a comparison of a first visualization 2000 prepared without process 1900 and a second visualization 2002 prepared by applying process 1900. In the first visualization 2000, several steps are shown as a result of the voxel representation (steps between levels of the voxel grid). Advantageously, the second visualization 2002 prepared by applying process 1900 shows a smooth modified bone surface without such artifacts. This allows display of a representation of the cut bone surface with a smooth surface as may be expected by the user (e.g., surgeon) to result from the bone modification. Plan-dependent visualization techniques as described herein thereby provide technical solutions in the field of graphical visualization techniques for computer-assisted surgical operations, including with respect to robotic surgery systems.

Referring now to FIG. 22, a flowchart of a process 2200 for providing a visualization using procedural geometry is shown, according to some embodiments. The process 2200 can be executed by the can be executed by execution by one or more processors of instructions stored in non-transitory computer-readable media, e.g., by the system 10 for example by or using the navigation system 22 (e.g., by the GPU 28).

At step 2202, a bone model and a planned resection are provided. The bone model can be provided as described above, for example based on segmentation of pre-operative images (e.g., MRI, CT, etc.) of a patients bone, based on a library of stored bone models, based on interoperative tracking of a probe contacting surfaces of the bone, etc. The planned resection can be provided based on results of a surgical planning workflow, for example provided via a graphical user interface of the system 10. The planned resection can be a surface (E.g., curved surface, plane) and/or volume having a planned pose (location and orientation) relative to the bone model. Data relating to the planned resection provided in step 2202 can include selection of a tool to be used in the planned resection, planned poses for the tool to be in while executing the planned resection, and/or other information relating to the tool to be used in the planned resection.

At step 2204, a grid bounding box is defined based on the planned resection. Step 2204 can include generating a grid, for example divided into axis-aligned bounding box voxels (e.g., in three-dimensions) based on the planned resection. The grid can be sized to encompass the planned resection (e.g., with a surrounding region of interest), for example provided as the minimum size suitable for including the planned resection and a surrounding region of interest. In some embodiments, the grid is oriented based on the planned resection, for example as described above with reference to FIG. 14. Step 2204 can include providing each voxel with a linked list to which procedural geometry data can be added.

At step 2206, grid voxel parameters are defined based on the planned resection. For example, voxel parameters such as voxel size, etc. can be determined as a function of the planned resection, for example so as to provide sufficient accuracy, resolution, etc. while improving computational efficiency, based on the shape of the planned resection.

At step 2208, procedural geometry parameters are defined based on at least one cutting tool and a pose for the at least one cutting tool associated with the planned resection. Data relating to the planned resection provided in step 2202 can include information on the tool to be used, which can be associated in step 2208 with a particular procedural geometry. For example, use of a burr of a particular size can be planned for use in the planned resection, and step 2208 can include defining procedural geometry to include a sphere having a radius of the burr indicated for the planned resection. As another example, use of a router-cutting tool can be indicated for the planned resection, in which scenario step 2208 can include defining procedural geometry to include a half-capsule shape of a size corresponding to the identified router-cutting tool, with a planned orientation of the tool used to orient the half-capsule shape in the procedural geometry. Various such examples are possible as appropriate to represent different tools, different sizes of tools, different orientations of tools, etc. that may be used. The procedural geometry parameters can thus be dynamically assigned based on the planned resection to best represent the particular tool(s) selected for use in a particular planned resection.

Figure 23:
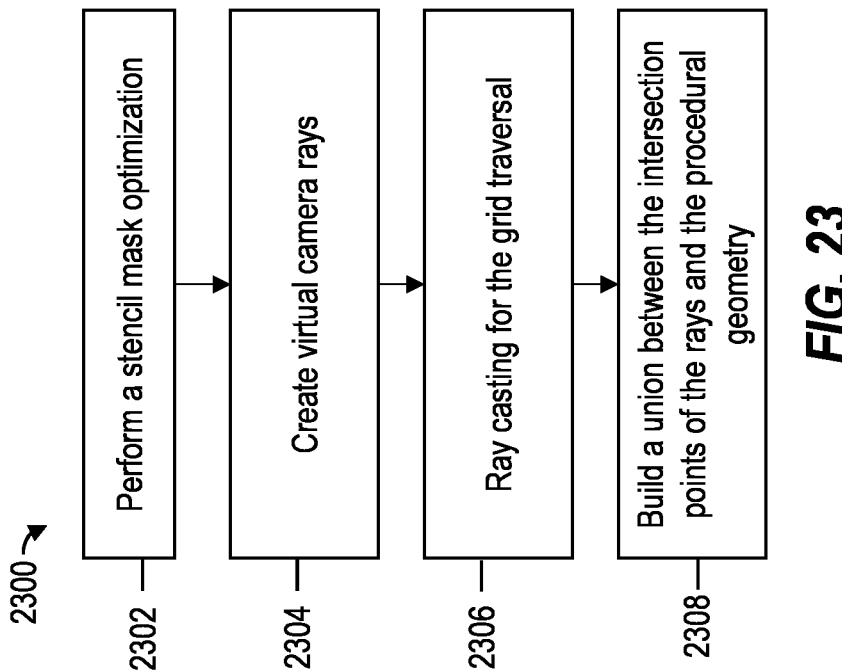
FIG. 23 is another flowchart relating to generating a visualization using procedural geometry, according to some embodiments.

At step 2210, a visualization of execution of the planned resection is generated using the bone model, the grid bounding box, the grid voxel parameters, and the procedural geometry. Step 2210 can include a ray-casting and/or CSG operation, for example as shown in FIG. 23 and described in detail with reference thereto below. Step 2210 can include providing surgical guidance and navigation by updating the visualization as the planned resection is executed, based on tracking of the tool, such that the visualization shows actual execution of the resection relative to the planned resection and the bone model. For example, positions taken by the tool during execution of the resection can be represented in the procedural geometry. Advantageously, the visualization is adapted to details of the planned resection, including the tool to be used in executing the planned resection, such that the visualization can accurately represent the planned resection (and execution of the planned resection based on tracking data) in a manner that smoothly represents cuts executed by the tool without artifacts that might otherwise be left by a rasterization approach. Accordingly, the process 2200 may be particularly well-adapted to providing visualizations for curved tools (e.g., spherical burrs) and/or curved resections, for example for guidance of surgical operations on shoulders or hips.

Process 2200 can be executed for different planned resections, for example such that the procedural geometry parameters are updated in accordance with the different planned resections. For example, a first planned resection can be associated with first procedural geometry parameters and guidance for the first planned resection can be provided using the first procedural geometry parameters. A surgical operation can then also include a second planned resection associated with second procedural geometry parameters (e.g., due to use of a second tool, based on a different orientation of the tool when executing the second resection relative to the first resection, etc.), such that the procedural geometry parameters can be updated from the first procedural geometry parameters to the second procedural geometry parameters for use in providing guidance for the second planned resection. Parameters used in visualization are therefore plan-dependent, i.e., variable based on planned resections of a surgical plan.

Referring now to FIG. 23, a process 2300 for providing a visualization using procedural geometry is shown, according to some embodiments. The process 2300 can be executed by the can be executed by execution by one or more processors of instructions stored in non-transitory computer-readable media, e.g., by the system 10 for example by or using the navigation system 22 (e.g., by the GPU 28). Process 2300 can be executed as part of step 2210 of process 2200, in some embodiments.

At step 2302, a stencil mask optimization is performed. The stencil mask optimization can include determining area for ray casting, for example an area where the bone model overlaps the planned resection. Step 2302 can include proving the stencil mask (stencil buffer) to regulate the number of rays that will be cast, for example according to the solution to an optimization problem that minimizes the number of rays or optimizes some other objective to improve computational efficiency of process 2300.

At step 2304, a virtual camera rays are created. The virtual camera rays extend from the point of view of a virtual camera viewing the bone model and planned resection, for example the viewpoint of a virtual camera as mentioned above with reference to FIG. 11. Step 2304 can include creating sufficient virtual rays to view the area defined by the stencil mask from step 2302, for example with each ray associated with a pixel of a display screen for the visualization. Each ray may have a direction defined by the corresponding pixel's coordinate in screen space, and is oriented to intersect a procedural geometry grid (e.g., from process 2200).

At step 2306, ray casting is performed. The rays created in step 2304 are cast and traverse the procedural geometry grid (e.g., the grid generated according to process 220). Various approaches for ray casting grid traversal can be implemented. Ray casting can determine the points at which the procedural geometry (e.g., surfaces thereof) intersect the rays.

At step 2308, a union between the intersection points of the rays and the procedural geometry is built. Step 2308 can include determining area associated with intersections of the rays with the procedural geometry. For example, where the procedural geometry represents tracked positions of a tool during execution of a resection, the union between the intersection points of the rays and the procedural geometry can represent the resection made by the tool. The union can then be used for selecting the colors of pixels associated with various rays. In some embodiments, the output of step 88 can then be provided to block 44 of FIG. 8 for CSG composition or other steps for providing a final visualization via a display screen. Accordingly, the procedural geometry (e.g., defined in a plan-dependent manner in process 2300) can be used in a ray-casting approach to facilitate visualization of surgical operations.

Figure 24:
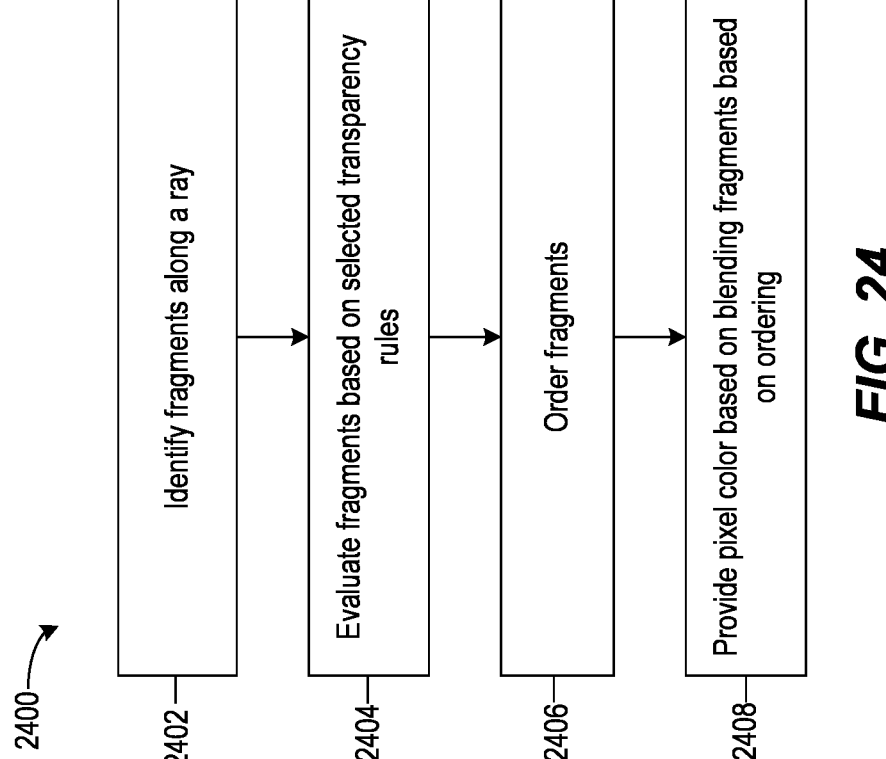
FIG. 24 is a flowchart of a process for providing visualizations with transparency, according to some embodiments.
Figure 25:
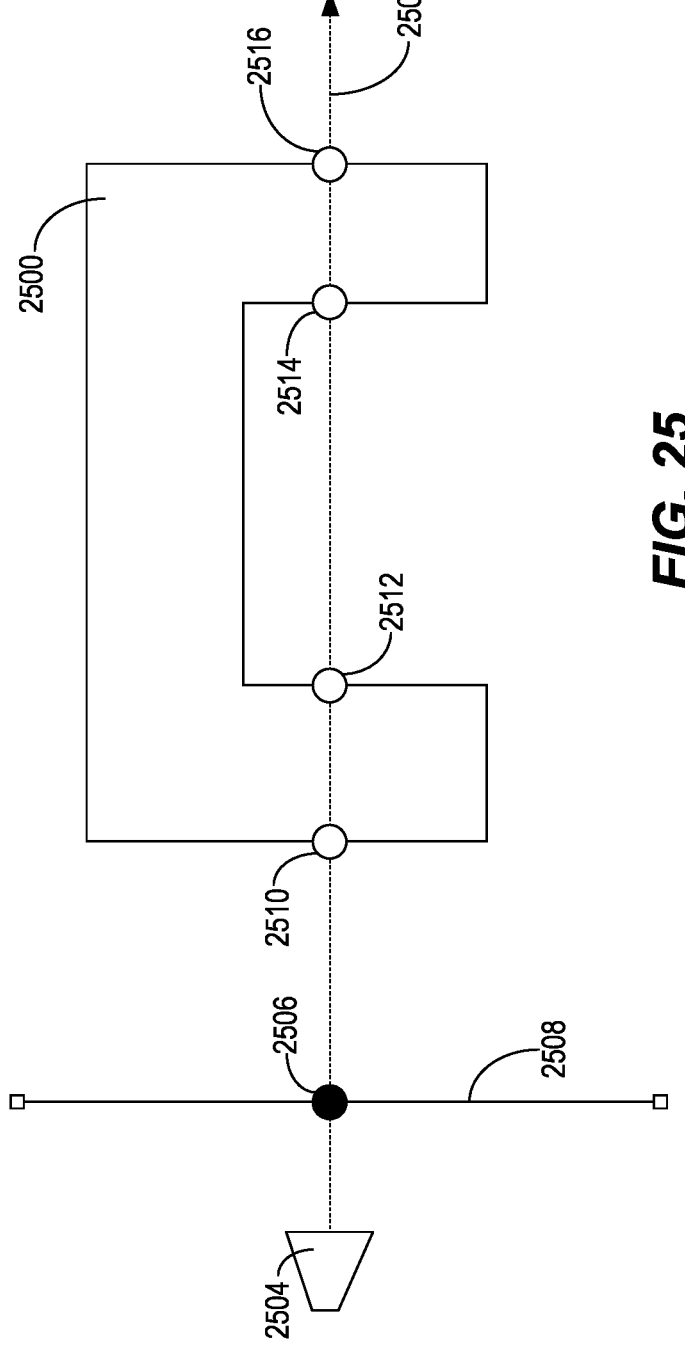
FIG. 25 is a diagram illustrating features for providing visualizations with transparency, according to some embodiments.

Referring now to FIGS. 24-25, teachings relating to providing transparency of visualizations for surgical planning and navigation are shown, according to some embodiments. FIG. 24 illustrates a process 2400 and FIG. 25 provides an example illustration to facilitate understating of process 2400. The process 2400 can be executed by the can be executed by execution by one or more processors of instructions stored in non-transitory computer-readable media, e.g., by the system 10 for example by or using the navigation system 22 (e.g., by the GPU 28). The process 2400 can be executed in combination with any of the various other processes and approaches described herein, for example when transparency of one or more surfaces or objects represented in the visualizations herein is desired (e.g. transparency of a bone model, transparency of an implant, transparency of a cutting tool, transparency of a planned resection, etc.).

At step 2400, fragments are identified along a ray. FIG. 25 illustrates an example of identification of fragments of an object 2500 along a ray 2502. The ray 2502 is cast from a virtual camera 2504 and is associated with a pixel 2506 at plane 2508. Due to the geometry of the object 2500, the ray 2502 crosses a border of the object 2500 four times, with the crossing points identified as fragments. In particular, as shown in FIG. 25, process 2400 would identify four fragments: first fragment 2510, second fragment 2512, third fragment 2514, and fourth fragment 2516. Various other geometries will result in other fragments being identified, with a ray—in most scenarios—identifying a fragment at least at a front surface of an object and a back surface of the object, potentially with intermediate fragments for hollow objects, objects intersected by other objects, etc.

At step 2404, the fragments are evaluated based on selected transparency rules. The transparency rules can indicate which fragments should be kept and/or discarded to provide desired transparency visualizations. In the example of FIG. 24, an example set of transparency rules may indicate that the second fragment 2514 and the third fragment 2516 should be discarded to avoid cluttering a visualization with representation of the internal surfaces, for example by providing a rule based on relationships between multiple points (e.g., a rule to discard any point having a point both closer and further from the camera 2504 to said point). Step 2404 can also include associating an opacity level (e.g., completely opaque, 60% opacity, 20% opacity, complete transparency, etc.) to different fragments. Various rules are implementable in step 2402 depending on the particular visual effects desired to be achieved using process 2400. Advantageously, such rules can be applied using results of step 2402 without prior knowledge or data stored with the object 2500 indicating which surfaces are front, back, interior, etc. In some embodiments, after passing through the evaluation of step 2404, fragments area appended to a linked listed for an order independent transparency algorithm.

At step 2406, fragments are ordered. Ordering the fragments can include determining the order in which the fragments are intersected by a ray. In the example of FIG. 25, step 2406 can include determining that the ray 2502 first intersects the first fragment 2510, then intersects the second fragment 2512, then intersects the third fragment 2514, then intersects the fourth fragment 2516, for example based on a determined depth of the fragments along the ray 2502. Step 2406 can determine that the first fragment 2510 is closer to the virtual camera 2504 than the last segment 2516. Various sorting and/or ordering operations can be executed in step 2406.

At step 2408, a pixel color is determined based on blending fragments based on ordering. For example, based on the transparency rules evaluated in 2404, a set of relevant fragments can be provided, with each fragment provided with an associated color (with the color being further based on a transparency level, in various embodiments). Based on the order of such fragments (e.g., whether a first fragment is in front of or behind a second fragment as determined in step 2406), the associated colors can be blended (combined, merged, etc.) to provide a color for the pixel associated with a ray. By repeating such operations for different rays cast across an object according to teachings described elsewhere herein, a visualization with transparent features can be provided, thereby enabling a user to see objects internal to other objects, internal features of objects, etc. in various embodiments.

Various visualizations can thereby be provided. With reference to FIG. 25, if fragment 2510 is assigned full opacity, the object 2500 will appear as a solid object without visualization of the other fragments. As another option, all fragments 2510-2516 may be assigned less than full opacity (e.g., 60% opacity), in which case the visualization can provide the ability to see all surfaces. As another option, the first fragment 2510 and the fourth fragment 2516 can be provided with partial transparency, while the second fragment 2512 and/or the third fragment 2514 is/are shown as opaque, facilitating a view of the internal structure of the object 2500. As another option, the fourth fragment 2516 can be provided as opaque while the first fragment 2510 is provided as transparent (e.g., 60% opacity), thereby facilitating a view of the back surface of the object 2500. Various such examples are possible, for example selectable by a user to facilitate viewing of features of interest in the visualizations contemplated by the present disclosure.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A method, comprising:
   providing a bone model and a surgical plan defining a planned cut relative to the bone model;
   orienting a voxel grid relative to the bone model based on the planned cut;
   obtaining tracking data indicative of positions of a cutting tool; and
   providing guidance for execution of the planned cut by generating a visualization based on the voxel grid and the tracking data.

2. The method of claim 1, wherein orienting the voxel grid relative to the bone model based on the planned cut comprises orienting a first dimension of the voxel grid orthogonal to the planned cut.

3. The method of claim 2, wherein orienting the voxel grid relative to the bone model further comprises orienting a second dimension and a third dimension of the voxel grid parallel with the planned cut.

4. The method of claim 1, wherein the surgical plan further defines an additional planned cut, the method further comprising:
   in response to completion of the planned cut, reorienting the voxel grid based on the additional planned cut; and
   providing guidance for the execution of the additional planned cut by generating an additional visualization based on the voxel grid and the tracking data.

5. The method of claim 4, wherein reorienting the voxel grid based on the additional planned cut comprises changing the voxel grid from a first orientation where a first dimension of the voxel grid is orthogonal to the planned cut to a second orientation where the first dimension of the voxel grid is orthogonal to the additional planned cut.

6. The method of claim 1, wherein generating the visualization based on the voxel grid and the tracking data comprises:
   representing, in the voxel grid and based on the tracking data, an accumulation of the positions the cutting tool as the cutting tool performs the planned cut; and
   determining voxels of the voxel grid shared by the bone model and the accumulation of the positions of the cutting tool;
   wherein the visualization comprises a representation of a surface of the bone model resulting from removal of virtual bone from the voxels shared by the bone model and the accumulation of the positions of the cutting tool.

7. The method of claim 6, wherein generating the visualization comprises smoothing the representation of the surface based on the planned cut by:
   obtaining an adjusted normal by adjusting a normal of the representation of the surface of the bone model in the voxel grid based on a normal of the planned cut; and
   shading the visualization using the adjusted normal.

8. One or more non-transitory computer-readable media storing program instructions that, when executed by one or more processors, cause the one or more processors to perform operations comprising:
   providing a bone model and a surgical plan defining a planned cut relative to the bone model;
   orienting the bone model relative to a graphics coordinate system based on the planned cut such that the planned cut is orthogonal to a first dimension of the graphics coordinate system, parallel to a second dimension of the graphics coordinate system, and parallel to a third dimension of the graphics coordinate system;
   generating a visualization of execution of the planned cut based on the graphics coordinate system, the bone model, and tracking data indicative of positions of a cutting tool during the execution of the planned cut.

9. The one or more non-transitory computer-readable media of claim 8, wherein the graphics coordinate system defines a voxel grid.

10. The one or more non-transitory computer-readable media of claim 9, wherein generating the visualization comprises determining voxels of the voxel grid shared by the bone model and an accumulation of the positions of the cutting tool; and wherein the visualization comprises a surface resulting from removal of bone by the cutting tool, wherein the operations comprise determining the surface based on the voxels shared by the bone model and the accumulation of the positions of the cutting tool.

11. The one or more non-transitory computer-readable media of claim 10, wherein the operations further comprise smoothing the surface based on a normal of the planned cut by shading the visualization using an adjusted normal, wherein the adjusted normal is a function of the normal of the planned cut and a normal calculated from a representation of a result of the execution of the planned cut in the graphics coordinate system.

12. A surgical system, comprising:

a tool operable to modify a bone;

circuitry programmed to:

define a visualization grid based on a planned bone modification; and generate, using the visualization grid, a visualization of progress of the tool in executing the planned bone modification based on tracking data indicative of positions of the tool.

13. The surgical system of claim 12, wherein the circuitry is further programmed to:

in response to an indication of completion of the planned bone modification, update the visualization grid based on a subsequent planned bone modification; and generate, using the updated visualization grid, a second visualization showing progress of the tool in executing the additional planned bone modification.

14. The surgical system of claim 12, wherein:

the visualization comprises a representation of a bone surface resulting from the progress of the tool in executing the planned bone modification; and the circuitry is programmed to obtain the representation of the bone surface by determining voxels of the voxel gird shared by the model of the bone and a sweep of the positions of the tool.

15. The surgical system of claim 12, wherein the circuitry is further programmed to smooth the representation of the bone surface based on the planned bone modification.

16. The surgical system of claim 12, wherein the circuitry is programmed to define the visualization grid by defining grid voxel parameters based on the planned bone modification.

17. The surgical system of claim 12, wherein the circuitry is further programmed to define bounding box for the visualization grid based on the planned resection.

18. The surgical system of claim 12, wherein the visualization grid comprises axis aligned bounding box voxels, each voxel associated with a linked list providing procedural geometry data.

19. The surgical system of claim 18, wherein the circuitry is programmed to provide the procedural geometry data based on a shape of the tool.

20. The surgical system of claim 18, wherein the circuitry is programmed to define the visualization grid based on the planned bone modification by orienting the visualization grid relative to the planned bone modification such that a dimension of the visualization grid is orthogonal to the planned bone modification.

21. The surgical system of claim 12, wherein the surgical system is further programmed to generate a visualization with transparency by providing a color for a pixel by:

identifying a front surface and a back surface intersected by a ray associated with the pixel; and providing a first opacity to the front surface and a second opacity to the back surface.

* * * * *